United States Patent
Wiessler et al.

[11] Patent Number: 5,622,936
[45] Date of Patent: Apr. 22, 1997

[54] TUMOR INHIBITING SACCHARIDE CONJUGATES

[75] Inventors: Manfred Wiessler, Heidelberg; Michael Dickes, Dossenheim, both of Germany

[73] Assignee: Deutsches Krebsforschungszentrum Stiftung des offentlichen Rechts, Germany

[21] Appl. No.: 499,522

[22] PCT Filed: Oct. 19, 1989

[86] PCT No.: PCT/EP89/01251

§ 371 Date: Jun. 19, 1990

§ 102(e) Date: Aug. 13, 1990

[87] PCT Pub. No.: WO90/04597

PCT Pub. Date: May 3, 1990

[30] Foreign Application Priority Data

Oct. 20, 1988 [DE] Germany .................. 38 35 772.0

[51] Int. Cl.⁶ .................. A61K 31/70; C07H 15/00
[52] U.S. Cl. .................. 514/25; 514/54; 514/118; 536/117; 536/17.9; 536/18.5
[58] Field of Search .................. 536/117, 17.9, 536/18.5; 514/118, 25, 54

[56] References Cited

U.S. PATENT DOCUMENTS

| | | | |
|---|---|---|---|
| 4,716,242 | 12/1987 | Engel et al. | |
| 4,739,095 | 4/1988 | Eibi. | |
| 4,849,513 | 7/1989 | Smith et al. | 536/27 |
| 5,015,733 | 5/1991 | Smith et al. | 536/23 |
| 5,055,459 | 10/1991 | Andersson et al. | 514/114 |
| 5,194,428 | 3/1993 | Agrawal et al. | 514/44 |

FOREIGN PATENT DOCUMENTS

| | | |
|---|---|---|
| 0098601 | 1/1984 | European Pat. Off. |
| 122386 | 6/1975 | Germany. |

OTHER PUBLICATIONS

*Chemical Abstracts*, No. 77679k, "Glycosyl Phosphites and Glycosyl Phosphonites" (vol. 69, 1968), p. 7279.
*Chemical Abstracts*, No. 25895f, "2,3,4,6–Tetra–O–acetyl–α,β–glucopyranosyl esters of N–aryl–N', N'–bis–2–chloroethyldiamidophosphoric acid" (vol. 81, 1974), p. 454.

*Primary Examiner*—Gary L. Kunz
*Assistant Examiner*—Kathleen Kahler Fonda
*Attorney, Agent, or Firm*—Venable, Baetjer, Howard & Civiletti

[57] ABSTRACT

The invention relates to a method for the preparation of glycoconjugates of phosphorus amides with the general formula

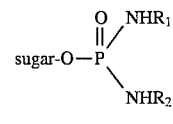

and

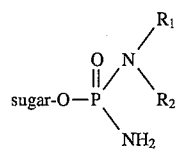

where the connection of the sugar with the phosphoric acid amide mustard residue, and the ifosfamide mustard residue, respectively, occurs preferably in the 1-position, and where $R_1$ and $R_2$; which can be the same or different, denote hydrogen, lower $C_1$–$C_4$ alkyl or $C_1$–$C_6$ haloalkyl and whereas sugar there can be present mono-, di-, or polysaccharides in all existing isomeric and enantiomeric forms, wherein in a known way protected brominated sugars are conjugated with the respective phosphorus compounds, and freed of the protective residues, and to the use of said compounds as anti-tumour drugs.

10 Claims, 16 Drawing Sheets

FIG.1
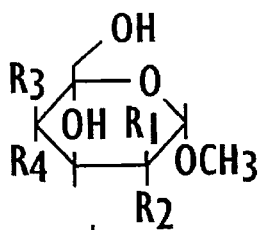
| R1 | R2 | R3 | R4 | |
|----|----|----|----|---|
| H  | OH | H  | OH | Methyl-α-D-Glc |
| H  | OH | OH | H  | Methyl-α-D-Gal |
| OH | H  | H  | OH | Methyl-α-D-Man |
↓ BnCl / Base
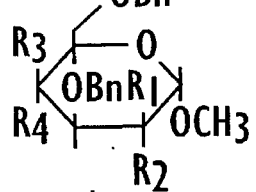
| R1 | R2 | R3 | R4 | |
|----|----|----|----|---|
| H  | OBn | H  | OBn | 10 |
| H  | OBn | OBn | H  | 11 |
| OBn | H  | H  | OBn | 12 |
↓ $H^+$
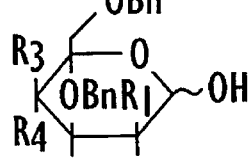
| R1 | R2 | R3 | R4 | |
|----|----|----|----|---|
| H  | OBn | H  | OBn | 13 |
| H  | OBn | OBn | H  | 14 |
| OBn | H  | H  | OBn | 15 |
↓ p-$NO_2$BzCl
   o.
   Ph-N=C=O
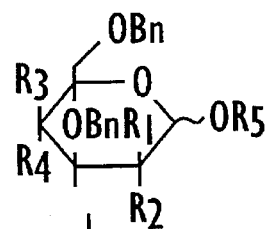
| R1 | R2 | R3 | R4 | R5 | |
|----|----|----|----|----|---|
| H  | OBn | H  | OBn | CO-Ph-$NO^2$ | 16 |
| H  | OBn | OBn | H  | CO-NH-$Ph_2$ | 17 |
| OBn | H  | H  | OBn | CO-Ph-$NO^2$ | 18 |
↓ HBr
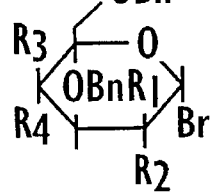
| R1 | R2 | R3 | R4 | |
|----|----|----|----|---|
| H  | OBn | H  | OBn | 19 |
| H  | OBn | OBn | H  | 20 |
| OBn | H  | H  | OBn | 21 |

FIG. 2
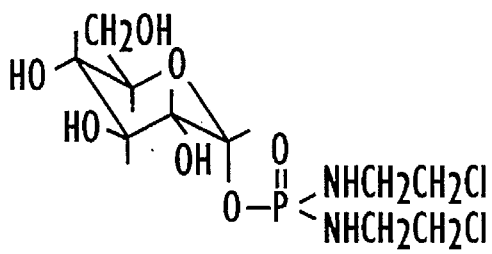
<u>28α</u>
Glc-α-IPM
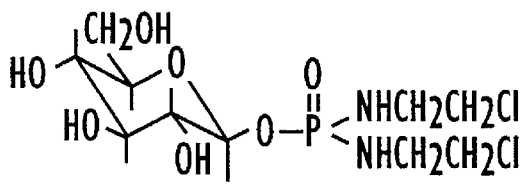
<u>28β</u>
Glc-β-IPM
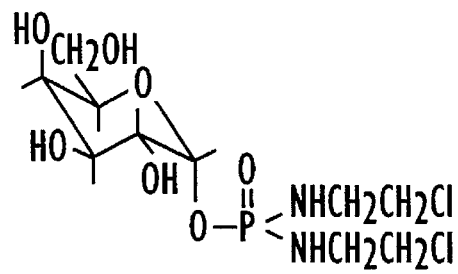
<u>29α</u>
Gal-α-IPM
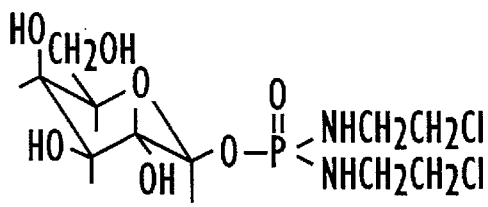
<u>29β</u>
Gal-β-IPM
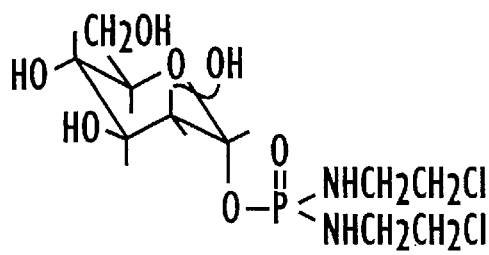
<u>30α</u>
Man-α-IPM
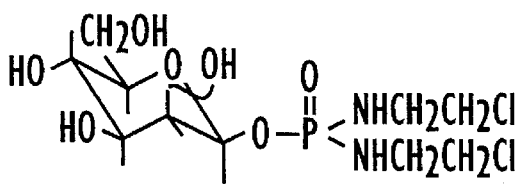
<u>30β</u>
Man-β-IPM

|    | R1  | R2  |
|----|-----|-----|
| 31 | H   | OBn |
| 32 | OBn | H   |

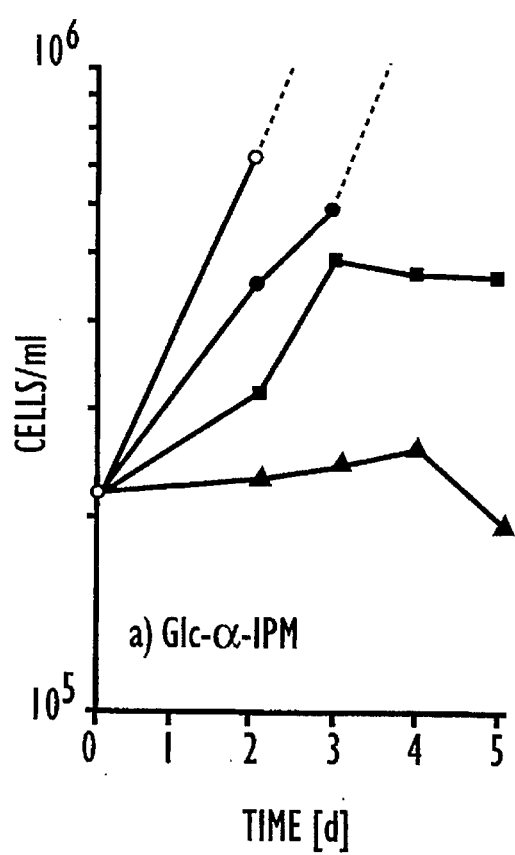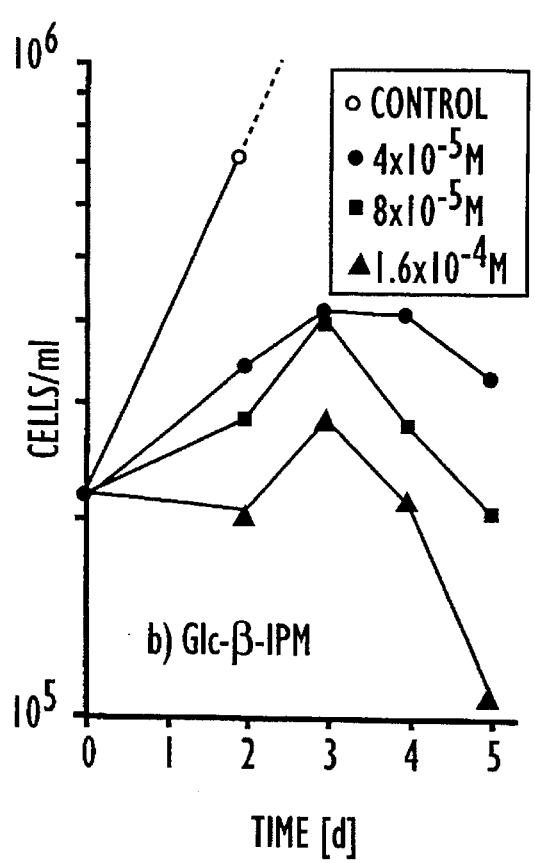

(a) IC26

(b) IC32

(c) IC39

● Glc-α-IPM
○ Glc-β-IPM
■ Gal-α-IPM
□ Gal-β-IPM
▲ Man-α-IPM
△ Man-β-IPM

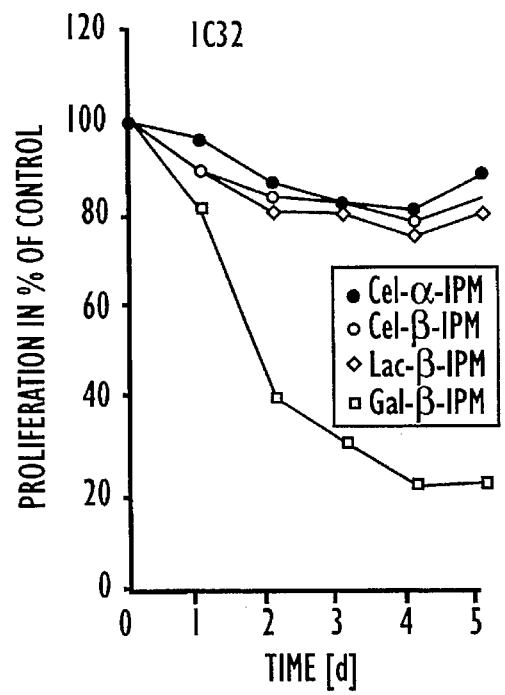 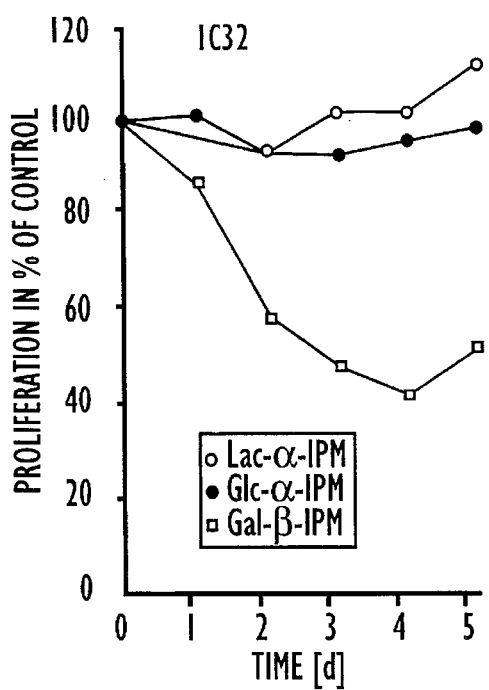
FIG. 10a
FIG. 10b

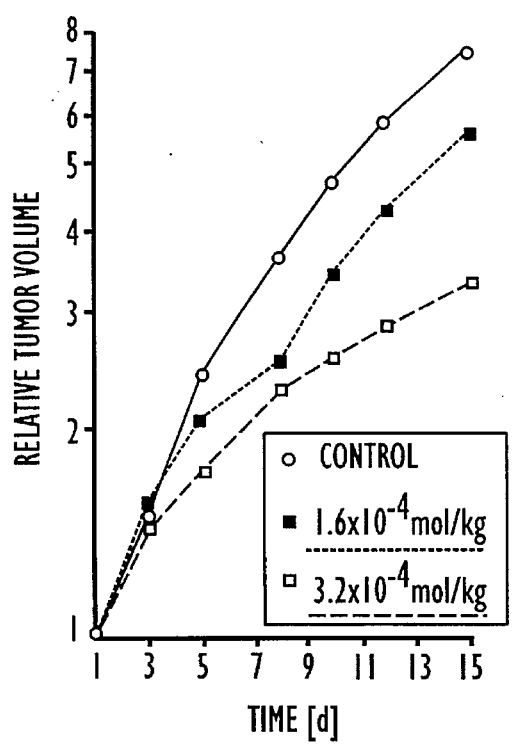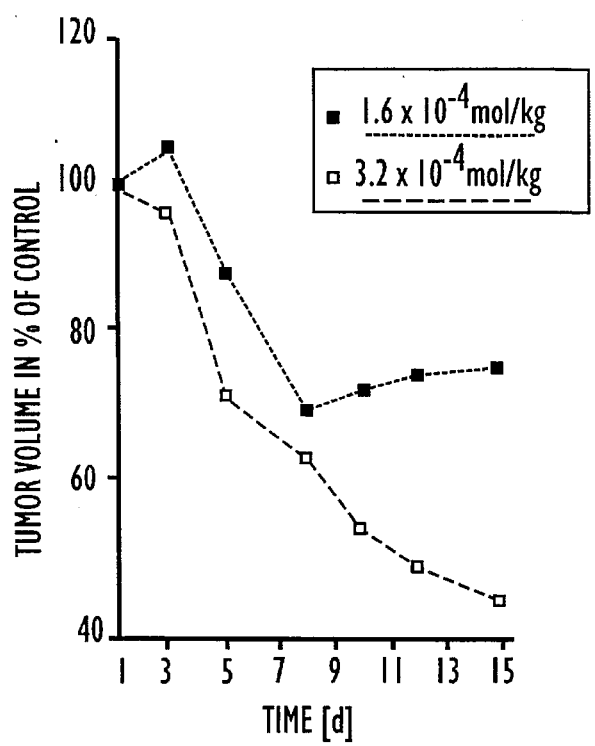
FIG.13a
FIG.13b

TUMOR INHIBITING SACCHARIDE CONJUGATES

BACKGROUND OF THE INVENTION

In the Federal Republic of Germany, mortality due to cancer ranks second, following cardiovascular diseases, in mortality statistics. Besides surgery and radiation, anti-neoplastic chemotherapy has nowadays become an established cancer therapy.

In spite of excellent surgical technique, improved radiation therapy, and many newly developed chemotherapeutic agents, in the last years it was not possible to improve the heilungsrate of malignant tumors, although very good results have been achieved with single kinds of tumors, as f.i. Hodgkin lymphoma (morbus Hodgkin).

There is, therefore, still a need to render possible fundamental improvements in chemotherapy, based on steadily increasing knowledge on the biochemistry of the tumor cell.

The main object in developing of new anti-neoplastic chemotherapeutic agents is to improve the selectivity, and thus to decrease undesired side effects.

Although meanwhile many biochemical differences between the tumor cell and the normal cell are known, these differences are not too significant.

Many of the agents used at present therefore already has a certain selectivity, and thereby an useful therapeutic index, but there is still a long way to go to obtain absolute selectivity.

One possibility to reach that goal is the use of "prodrugs", i.e. drugs which are activated in a particular way at the site or inside the target cell, or which are detoxified with particular efficiency by non-target cells. Following another approach one tries to direct the drug to the site of or into the target cell or at least to enrich it there ("drug targeting").

Many concepts of drug targeting are based on a specific binding of a drua to the target cell or cn different uptake mechanisms of non-target and target cell. Also quantitative differences can be utilized in this respect.

By using the hybridoma technique (Köhler and Milstein, 1975, Nature 256:495) it is f.i. possible to produce specific monoclonal antibodies (MAB's) and with their help to recognize tumor-associated antigens (TAA's).

The glycoside esters to be prepared can be obtained by known methods, in particular by the further modified Koenigs-Knorr reaction or the imidate method.

A summary for such Methods, and of stereo-selective glycosylation, for which at present, depending on the stereochemistry of the linkage desired, there are three basic methods available, is given in particular in Paulsen, 1984, Chem. Soc. Rev. 13: 15.

It is known, though, that not every linkage desired can be prepared stereoselectively, despite the many glycosylation methods available. Every glycosyl transfer presents as a unique problem, and there are often no universal reaction conditions (Schmidt, 1986, Angew. Chem. 98: 213).

SUMMARY OF THE INVENTION

Therefore, the present inventions relates to glycoconjugates of certain, effective anti-tumor agents to be used as anti-neoplastic agents largely preserving the activity of those agents, but strongly diminishing their toxicity.

BRIEF DESCRIPTION OF THE DRAWINGS

FIG. 1 shows the synthesis of benzylated bromoglycoses.

FIGS. 2A–2F show the structures of deprotected diastereomeric glycosyl-IPM conjugates.

FIG. 8a shows the effect over time of Glc-α-IPM on the proliferation of retrothelial sarcoma cells in vitro.

FIG. 8b shows the effect over time of Glc-β-IPM on the proliferation of retrothelial sarcoma cells in vitro.

FIG. 9a- 1 C26; FIG. 9B - 1 C32; and FIG. 9c- 1 C39.

FIGS. 10a and 10b show the effect over time of disaccharide IPM conjugates on the proliferation of mammary tumor cell line 1C32. FIG. 10a shows the results with Cel-α-IPM, Cel-β-IPM, Lacβ-IPM and Gal-β-IPM. FIG. 10b shows the results with Lac-α-IPM, Glc-α-IPM and Gal-β-IPM.

FIG. 11a shows the results using cell line Eb and Gal-α-IPM. FIG. 11b shows the results using cell line Eb and Gal-β-IPM. FIG. 11c shows the results using cell line ESb⁻ and Gal-α-IPM. FIG. 11d shows the results using cell line Esb⁻ and Gal-β-IPM.

FIG. 12a shows the results with female mice. FIG. 12b shows the results with male mice.

FIGS. 13a and 13b show the growth of the transplanted tumor 1C32 in controls and when given various doses of Gal-IPM. FIG. 13a shows the relative tumor volumes. FIG. 13b shows the tumor volumes as a percent of control.

DETAILED DESCRIPTION OF THE INVENTION

Figure 3:
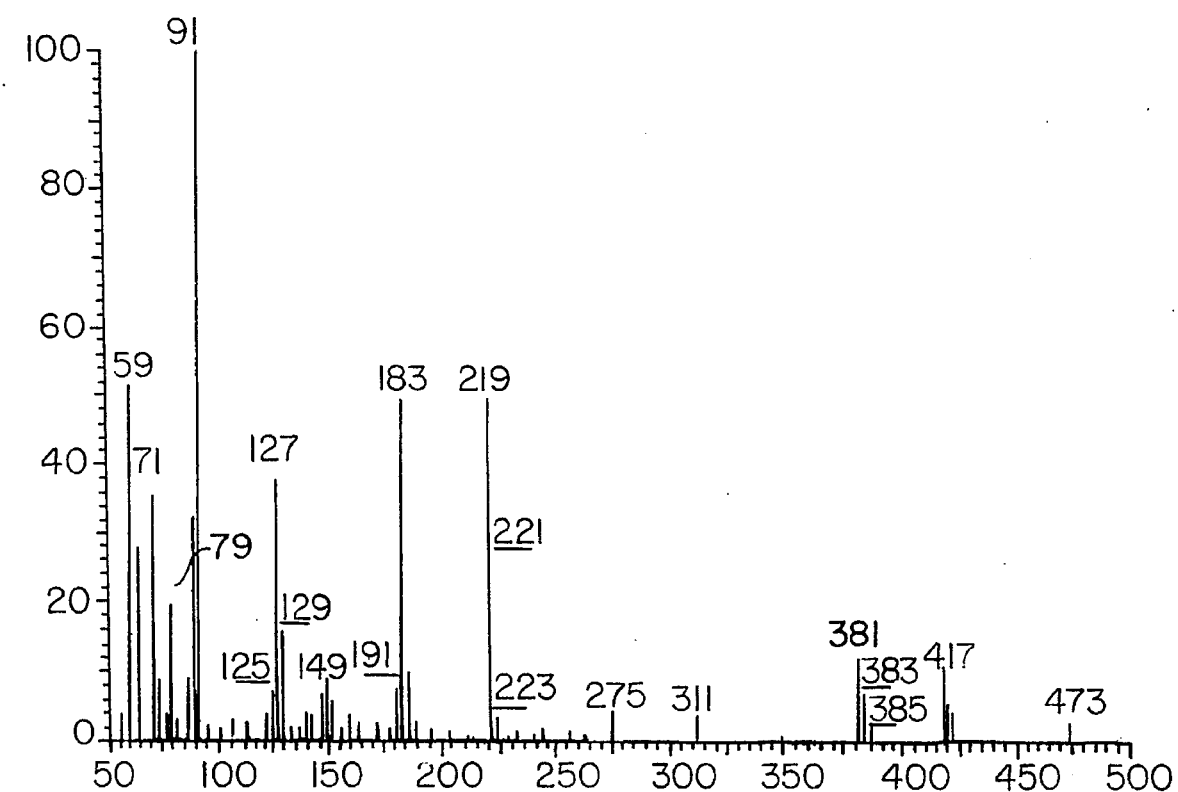
FIG. 3 shows the FAB $^1$H-NMR spectrum (negative) of Glc-β-IPM.

As typical examples, conjugates corresponding to the following general formula have been prepared:

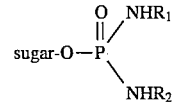

1 and

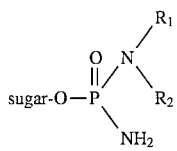

where linkage of the sugar to the phosphoric acid amide-lost residue preferably occurs in the 1-position. Galactose, mannose, glucose, mannan, galactan, glucan, and branched-chain sugars, particularily in position 3 and 6, are to be named as most important sugars, while, however, basically all sugars can be employed.

$R_1$ and $R_2$ can be the same or different, and represent as follows: hydrogen, lower $C_1$–$C_4$ alkyl, $C_1$–$C_6$ halogenoalkyl, preferably $C_1$–$C_4$ halogenoalkyls, and in particular $C_2$ halogenoalkyl.

All protective groups customary with OH-groups can be employed as protective groups, f.i. benzyl, acetyl, trityl groups, and they are split off, too, in a known way, enzymatically, by hydrogenolysis, under acidic or alkaline conditions.

Generally, the glycosylically linked phosphamide mustard and ifosfamide mustard, desired and used according to the present invention, can be prepared as follows:

The units to be linked, the phosphorus compounds can be prepared according to the protocol by Lorenz and Wießler, 1985, Arch. Pharm. 318: 577.

Each of these two compounds can be obtained with protected brominated saccharides according to the protocol illustrated by the example of compound 28 β,glucose-β IPM, and the disaccharide compound 50 and 51, according to the accompanying FIGS. 1 and 2, resp..

A protected sugar A is reacted with a phosphoric acid compound B by allowing both to react in a solvent, preferably a polar solvent, f.i. acetonitrile, $CH_2Cl_2$, or toluene, at a temperature ranging from 20° C. to 120° C. for a period from 1 h to 48 h, and with the addition of an auxiliary base, f.i. $Et_3N$, $Et(i-Prop)_2N$. The general protocol of the method can be depicted by the following schematic formula:

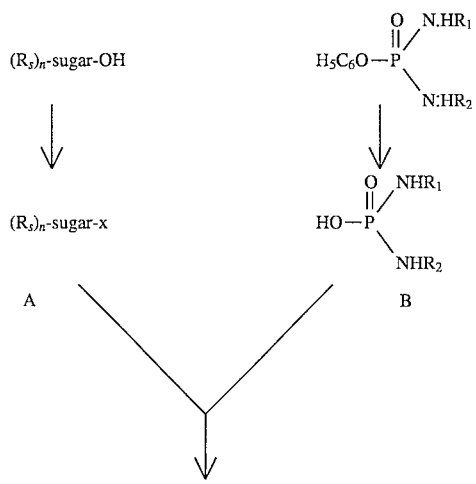

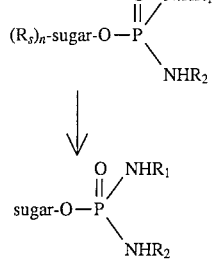

The reaction with ifosfamide occurred in a corresponding way.

$R_s$=a protective group, f.i. benzyl, x=a reactive group, f.i. bromine.

Starting from the 1-O-methyl pyranosides of glucose, galactose, and mannose, the corresponding 2,3,4,6-tetra-O-benzyl α-D-glycopyranosylbromides according to FIG. 1 can be prepared.

The benzylation occurs in a known way, f.i. in dioxane with benzyl chloride in the presence of KOH for methyl α-D-glucopyranoside, and -galactopyranoside, resp., while methyl α-D-mannopyranoside is reacted, f.i., in benzyl chloride/NaH. The benzylated methyl glycosides 10, 11, and 12 are subsequently hydrolyzed, f.i. with $H_2SO_4$/HOAc to give 13, and with HCl/HOAc to give 14 and 15, resp.. The compound 13 and the isomeric mannose 15 then can be derivatized to give the corresponding 2,3,4,6-tetra-O-benzyl 1-O-p-nitrobenzoyl D-glycopyranoses 16 and 18, both of which can be conveniently purified by recrystallisation. As this is not as easily possible for the p-nitrobenzoate of 2,3,4,6-tetra-O-benzylgalactose, in this case the derivatization with phenyl isocyanate in pyrimidine to give 2,3,4,6-tetra-O-benzyl 1-O-(N-phenylcarbamoyl) D-galactopyranose 17, which can be crystallized, is preferred (Kronzer and Schuerch, 1974, Carboh. Res. 33: 273).

The benzyl-protected α-bromohalogenoses 19, 20, and 21, formed, f.i., by treatment with HBr in $CH_2Cl_2$, and after usual processing, namely filtering off p-nitrosobenzoic acid, and aniliniumbromide, resp., and removal of excess HBr, are suitably used directly and without any further purification in the subsequent glycosylation reactions.

The glycosyl donors protected by benzyl groups now do not have a substituent at C-2 which could exert an influence directing the glycosylation. The reaction of the brominated sugars provided with protective benzyl groups with phosphamide and isfosfamide, resp., occurred in dichloromethane/triethylamine. The yield of the reaction of 16, 17, and 18 to 22, 23, and 24, as well as the ratio of the anomers and the eluent in the column chromatography is given in table 1. The separation as achieved by column chromatography.

TABLE 1

| | Yield (%) | α:β | EE:PE |
|---|---|---|---|
| 22 | 68 | 56:44 | 60:40 |
| 23 | 65 | 50:50 | 60:40 |
| 24 | 47 | 55:45 | 80:20 |

In the HPLC analysis the strong dependence of retention times on concentration as well as the significant tailing of the conjugates has to be noted. Ascertainment of structure and stereochemistry was done by $^1H$ and $^{13}C$ NMR spectroscopy.

For the preparation of larger amounts a technique was employed wherein by stereoselective synthesis one anomer is formed preferentially, thus making it possible to dispense with HPLC purification.

According to Schmidt, 1986, Angew. Chem. 98: 213, benzyl-protected O-glycosyl trichloroacetimidates can be employed for stereoselective syntheses. Synthesis of the was performed according to methods described in the literature, -starting from the tetra-O-benzylglycoses 13, 14, and 15.

Using potassium carbonate as base, the β-imidate 25β is obtained in a kinetically controlled reaction, with NaH a fast anomerization giving the thermodynamically more stable 25α is achieved. In an analogous manner, the galactosyl imidate 26α is obtained from 14, the mannosyl imidate 27α from 15. Compared to the bromine-activated benzyl glycosides these imidates have the advantage of greater stability; the can readily be recovered and stored.

Thus the imidates were reacted with IMP 4b under different reaction conditions. F.i. dichloromethane or acetonitrile were used as solvents, and $BF_3$, diethylether or HCl in dichloromethane as catalysts. The reaction occurred faster in $CH_3CN$ than in $CH_2Cl_2$. The mannosyl imidate 27α reacted selectively with 4b to give mannoside 24α.

The protected glycosides can be deprotected (freed of their protective groups) f.i. by catalytic hydrogenation with Pd/activated charcoal at room temperature. The course of the hydrogenation can be monitored with thin-layer chromatography. The detection can be done with methanolic sulfuric acid, however, detection with 4-(p-nitrobenzyl) pyridine reagent (NBP) is more sensitive.

After the reaction was completed the catalyst was removed by filtration, the filtrate was concentrated by rotation evaporation, and dried under high-vacuum. When using the pure anomeric glycosides 22, 23, and 24, the corresponding glycosides 28, 29, and 30 were obtained as pure anomers, too, (FIG. 2).

The corresponding phosphamide conjugates, as well as the conjugates of the derivatives according to the formula:

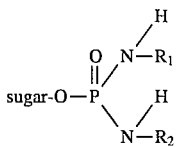

can be obtained in a corresponding manner.

Purification of the products forming as clear, colorless, highly viscous oils is not necessary. Should side-products be formed during hydrogenation, anyway, these can be removed by short column chromatography on silica (acetonitrile/methanol mixtures).

HPLC analysis permits to ascertain anomer ratios in the case of glucoside 28 and mannoside 30.

The identity of the compounds could be ascertained by FAB-MS and $^1$H-NMR spectroscopy. Moreover, the configuration of the sugar residues was confirmed by enzymatic reactions. As an example, the FAB spectrum (negative) of Glc-β-IPM is given in FIG. 3.

TABLE 2

Reactions of the trichloroacetimidates with IPM

| starting compound | solvent | reaction condition | product | yield | α:β |
|---|---|---|---|---|---|
| 25α | $CH_2Cl_2$ | RT, 1 d | 22 | — | |
| | | RF, 6 h | | 56% | 1:6 |
| | $CH_3CN$ | RT, 1 d | | low | |
| | | RF, 6 h | | 42% | 1:20 |

TABLE 2-continued

Reactions of the trichloroacetimidates with IPM

| starting compound | solvent | reaction condition | product | yield | α:β |
|---|---|---|---|---|---|
| 25β | $CH_2Cl_2$ | RF, 4 h | | 51% | 2:3 |
| | $CH_3CN$ | RF, 6 h | | 45% | 1:1.1 |
| 26α | $CH_2Cl_2$ | RT, 4 h | 23 | — | |
| | | RF, 8 h | | 48% | 2:5 |
| | $CH_3CN$ | RF, 6 h | | 42% | 1:3 |
| 27α | $CH_2Cl_2$ | RT, 4 h | 24 | — | |
| | | RF, 4 h | | 48% | |
| | $CH_3CN$ | RF, 6 h | | 47% | only α |

RT = room temperature

Figure 4:
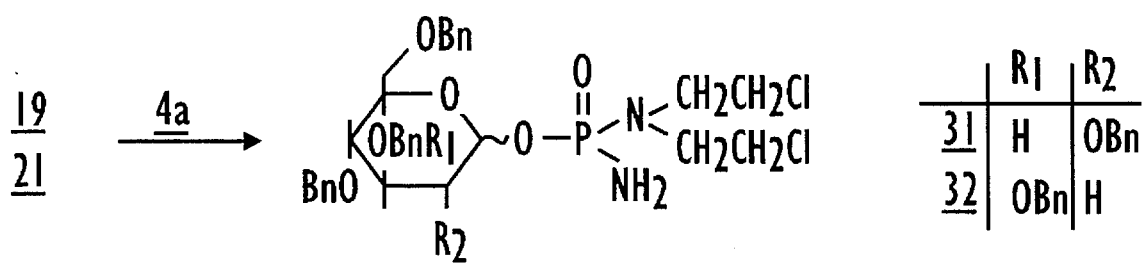
FIG. 4 shows the reaction of PM 4a with compounds 19 (2,3,4,6-tetra-O-benzyl α-D-glucopyranoside) and 21 (the respective mannosyl donor).

Using glycerol as a matrix, negative as well as positive FAB spectra gave significant information. From all 6 compounds signals of the negative molecule-peak ions (M-H)$^-$, and the positive-molecule-peak ions (M+H)$^+$ could be seen. In each case there occurred 3 peaks in a characteristical ratio, a phenomenon caused by the fact that the molecule contains 2 chlorine atoms, and that chlorine naturally occurs not as one pure isotope but as $^{35}$Cl and $^{37}$Cl in a ratio of 3:1, resulting in a ration of the isotope peaks of appr. 9:6:1. For the ions (M+H)$^+$ the expected values for m/e=383, 385, 387, for (M-H)$^-$ the corresponding values m/e=381, 383, and 385 are found. A characteristic fragment ion, namely that of the alkylating aglycone IPM was definitely shown with the signals m/e=221, 223, 225 for (IPM+H)$^+$, and m/e=219, 221, and 223 for(IPM-H)$^-$; here, too, the typical distribution of the isotope peaks is found. In FIG. 4, the two triplets of the ions (M-H)$^-$ and (IPM-H)$^-$ of Glc-β-IPM 28β are clearly visible. The signals m/e=91 and 183 are derived from the glycerol matrix used.

The attribution of the configuration at the anomeric center, as for the protected starting compounds, was possible with $^1$H-NMR by the typical couplings of the proton H-1 and its chemical shift; table 3 summarizes these parameters.

The PM 4a, isomeric with IPM, reacted with 2,3,4,6-tetra-O-benzyl α-D-glucopyranosid 19 and the respective mannosyl donor 21 in dichloromethane/triethylamine to give 2,3,4,6-tetra-O-benzyl D-glucopyranosyl N,N-bis-(2-chloroethyl) phosphoric acid diamide 31, and the 2-epimeric 32, resp., (FIG. 4).

TABLE 3

Chemical shifts and coupling of the anomeric proton of the deprotected monosaccharide-IPM conjugate

| | δ(H − 1) | $J_{1,2}$ | $J_{1,P}$ |
|---|---|---|---|
| 28α | 5.605 | 3.4 | 7.8 |
| 28β | 5.004 | 8.0 | 8.0 |
| 29α | 5.642 | 3.1 | 7.8 |
| 29β | 4.950 | 8.0 | 8.0 |
| 30α | 5.564 | 2.0 | 8.0 |
| 30β | 5.282 | 1.1 | 8.6 |

Figure 5:
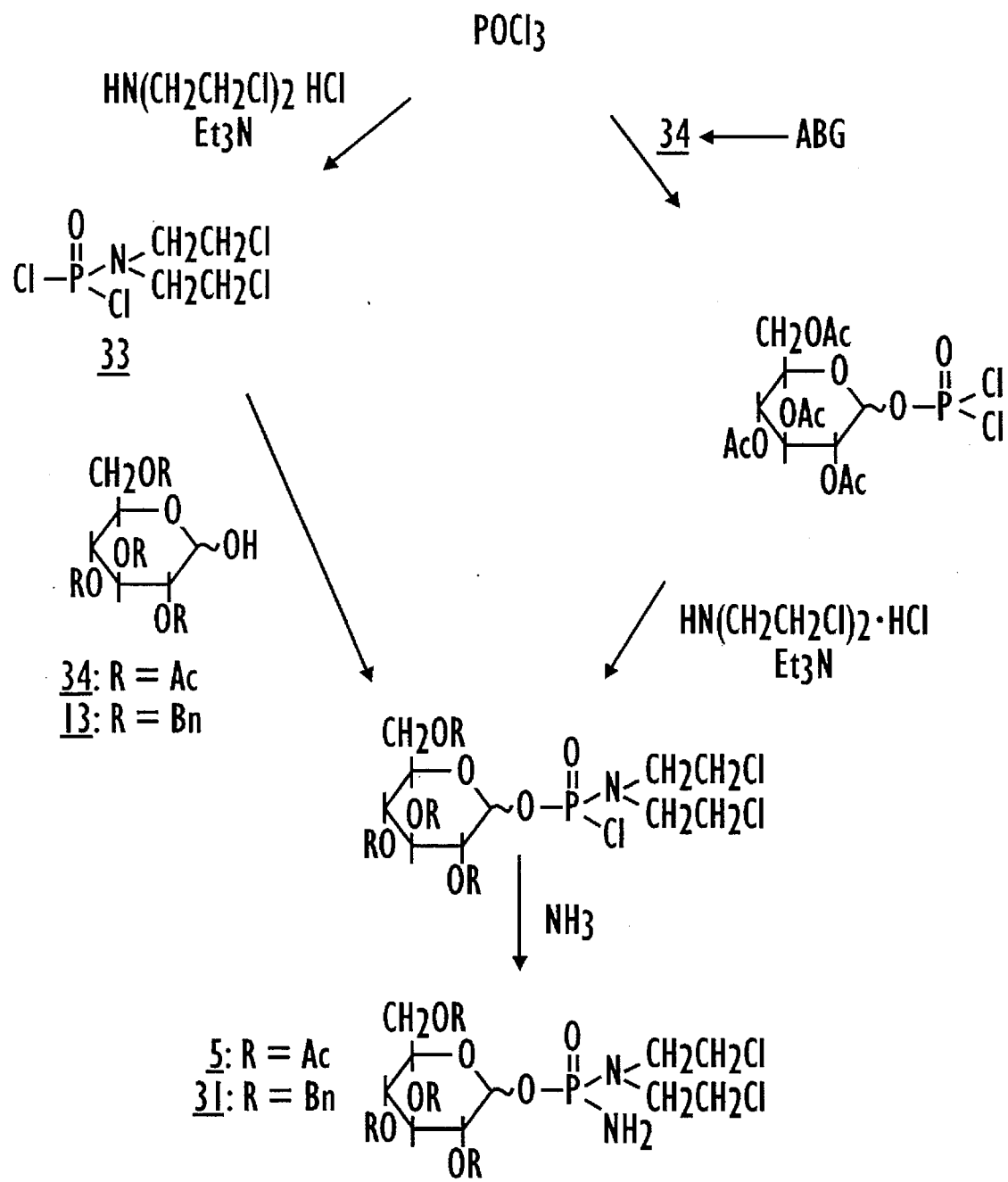
FIG. 5 shows possible synthetic pathways for glycosyl-PM conjugates 5 and 31.
Figure 6A:
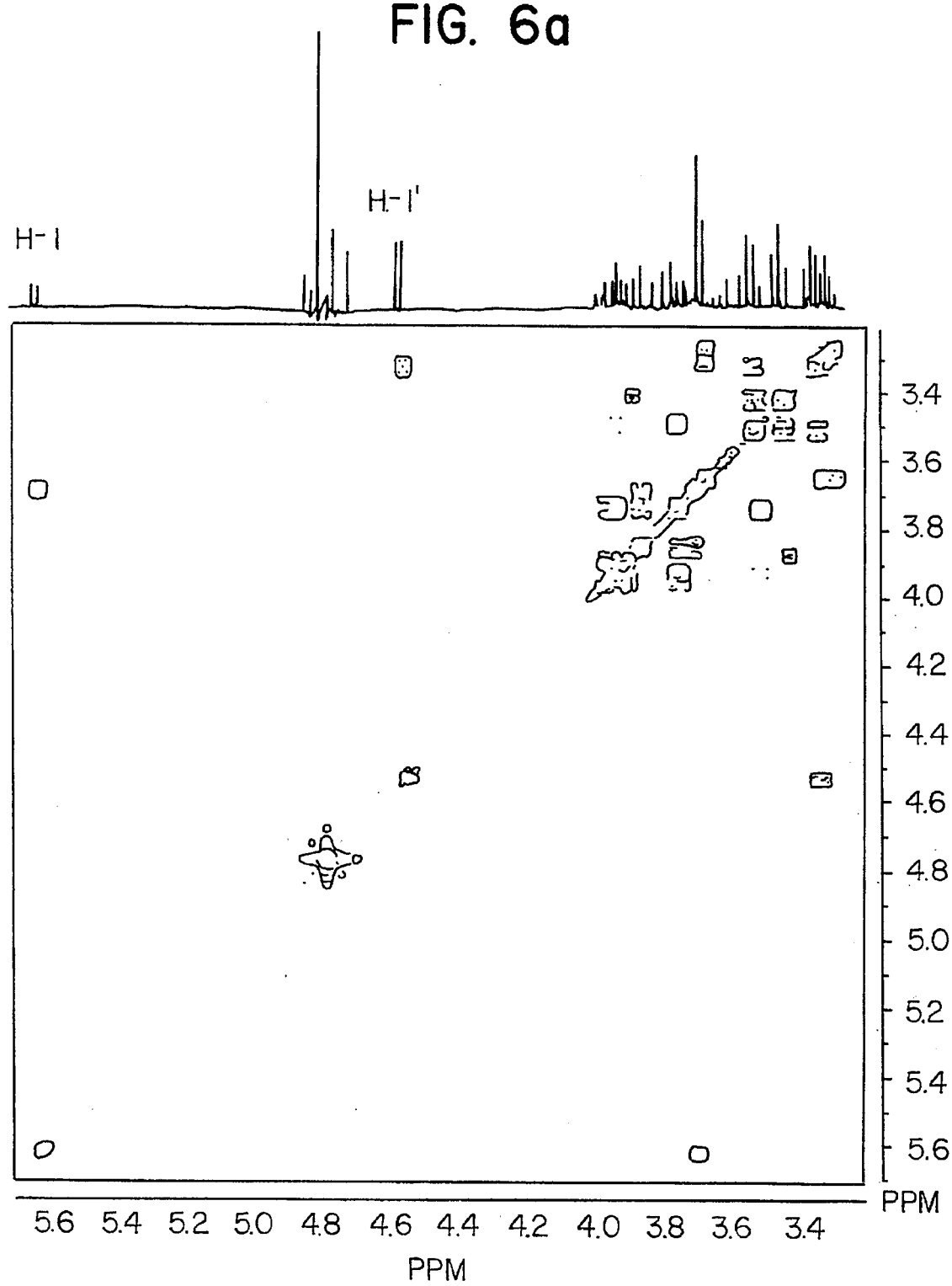
FIG. 6a shows the 500 MHz $^1$H-$^1$H-2D-NMR spectrum of the cellobiose conjugate 51α.
Figure 6B:
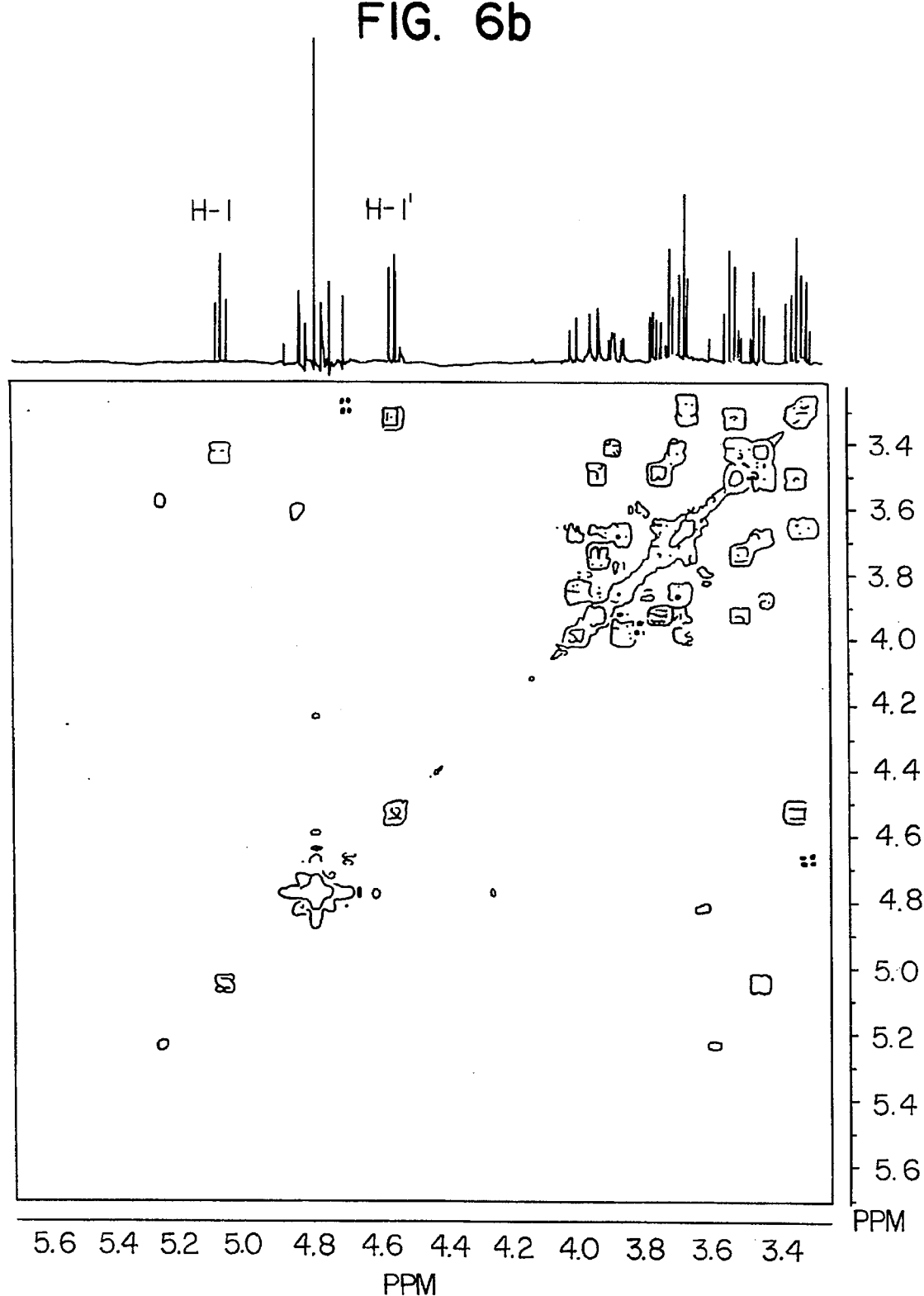
FIG. 6b shows the 500 MHz $^1$H-$^1$H-2D-NMR spectrum of the cellobiose conjugate 51β.

Still other ways of synthesis are possible for the preparation of the glycosyl-PM conjugates 5 or 31, as is shown in FIG. 5.

In an analogous way (examples 1 and 2) via the hepta-O-benzylglycoses 43 and 44

|    | $R_1$ | $R_2$ |
|----|-------|-------|
| 43 | OBn   | H     |
| 44 | H     | OBn   | the disaccharide-IPM conjugates 50 and 51 were obtained.

|    | $R_1$ | $R_2$ |
|----|-------|-------|
| 50 | OH    | H     |
| 51 | H     | OH    |

Table 4 shows the $^1$H-NMR data of the de-protected disaccharide conjugates.

TABLE 4

|      | δ(H – 1) | $J_{1,2}$ | $J_{1,P}$ | δ(H – 1') | $J_{1',2'}$ |
|------|----------|-----------|-----------|-----------|-------------|
| 50α  | 5.623    | 3.6       | 7.8       | 4.478     | 8.0         |
| 50β  | 5.049    | 8.0       | 8.0       | 4.473     | 8.0         |
| 51α  | 5.622    | 3.6       | 7.8       | 4.537     | 7.9         |
| 51β  | 5.044    | 8.0       | 8.0       | 4.532     | 8.0         |

Here, too, the identity of all four diastereomeric compounds was ascertained by 2D-NMR-COSY. FIG. *6a/6b* show as representative examples the 2D spectra of the de-protected cellobiose-IPM conjugate 51α and 51β.

Also in this case the structure of the sugar residue, i.e. lactose and cellobiose, resp., was confirmed by enzymatic reactions.

Figure 7:
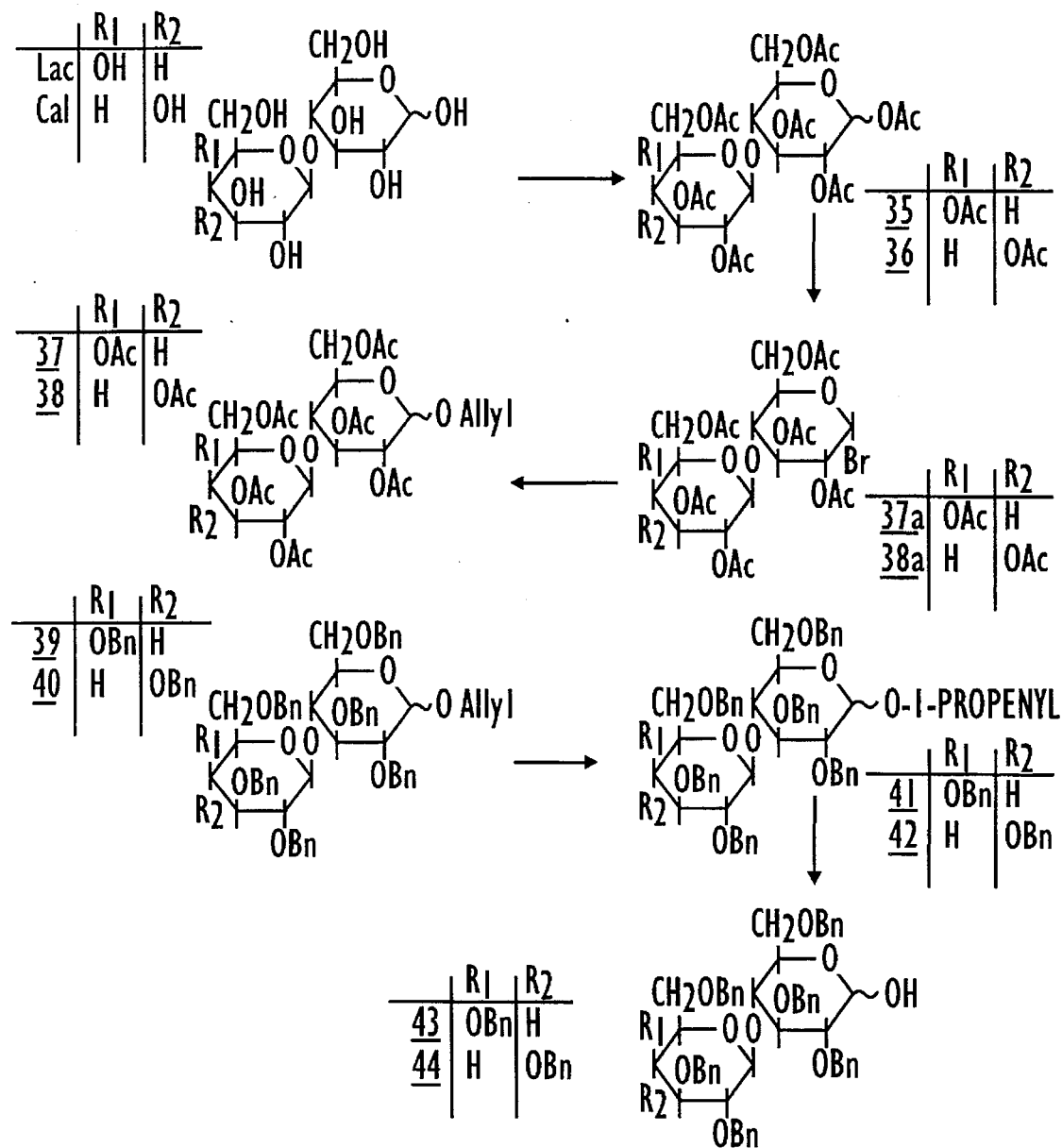
FIG. 7 shows a synthetic pathway for preparing 2,3,6,2', 3',4',6'-hepta-O-benzyl lactose (compound 43) and 2,3,6,2', 3',4',6'-hepta-O-benzyl cellobiose (compound 44).
Figure 9A:
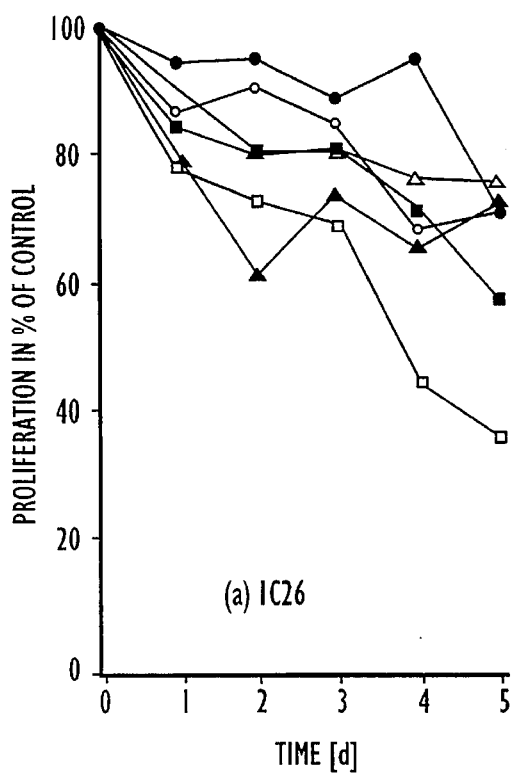
FIGS. 9a–9c show the effect over time of Glc-α-IPM, Glc-β-IPM, Gal-α-IPM, Gal-β-IPM, Man-α-IPM and Man-B-IPM on the proliferation of mammary tumor cell lines. The cell lines are.
Figure 9B:
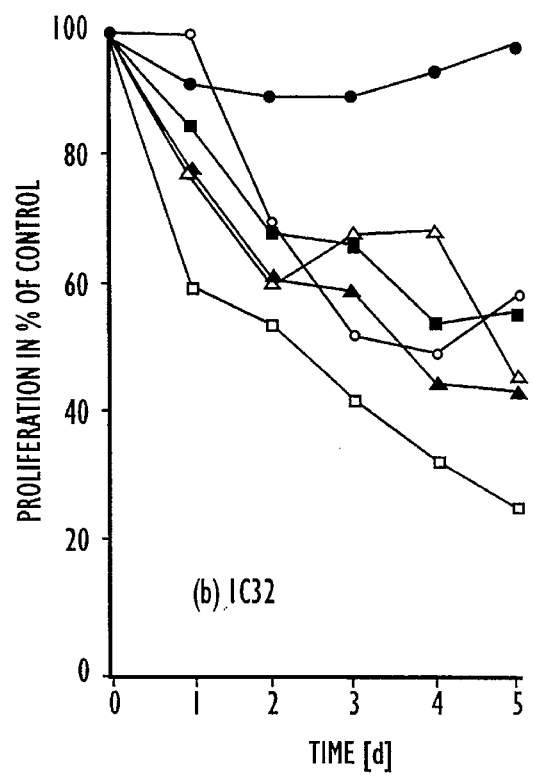
Figure 9C:
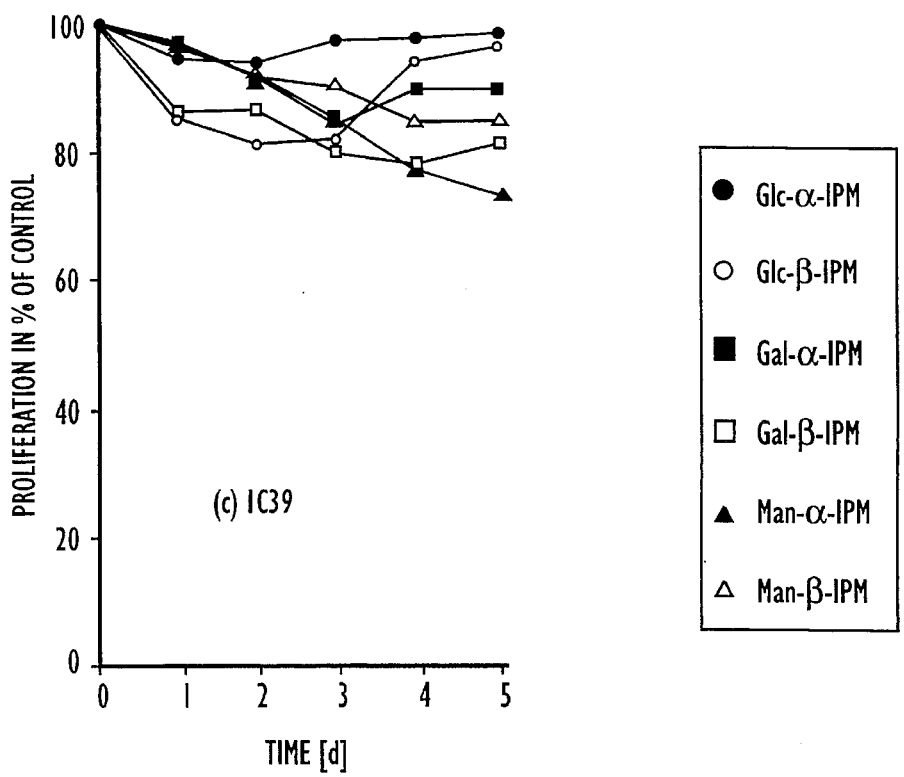
Figure 11A:
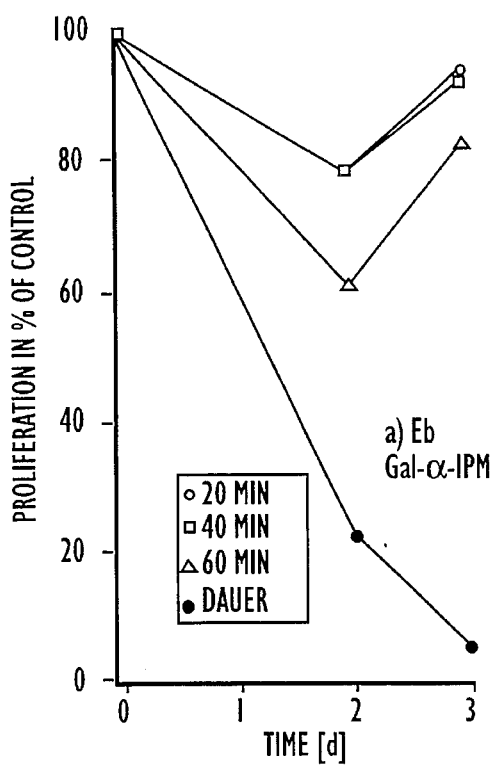
FIGS. 11a–11d show the dependence of proliferation of cell lines Eb and Esb⁻ on incubation times with Gal-α-IPM and Gal-β-IPM.
Figure 11B:
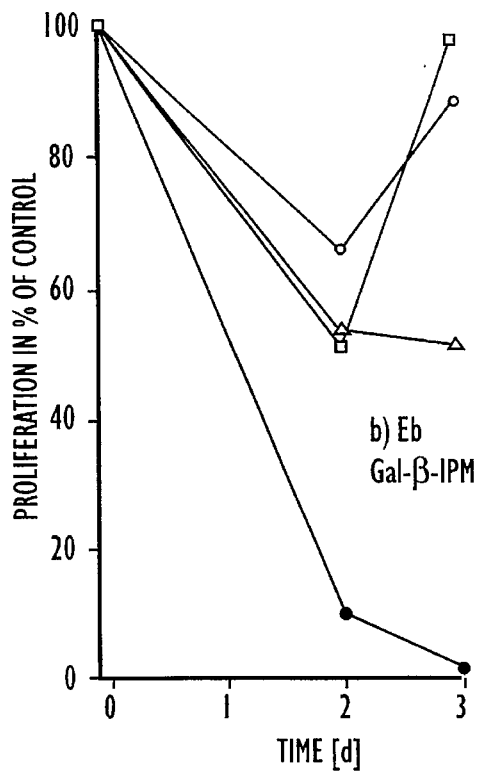
Figure 11C:
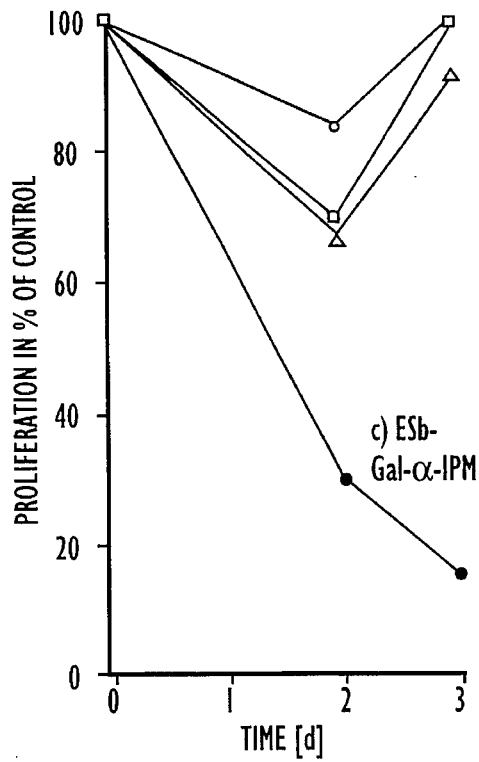
Figure 11D:
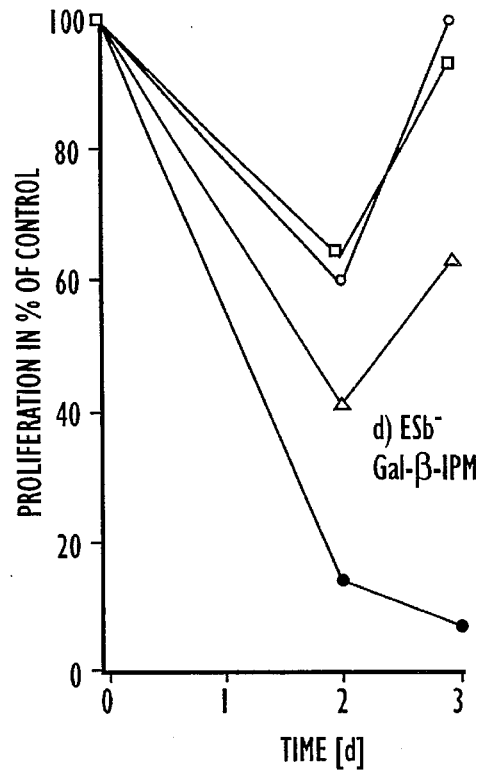
Figure 12A:
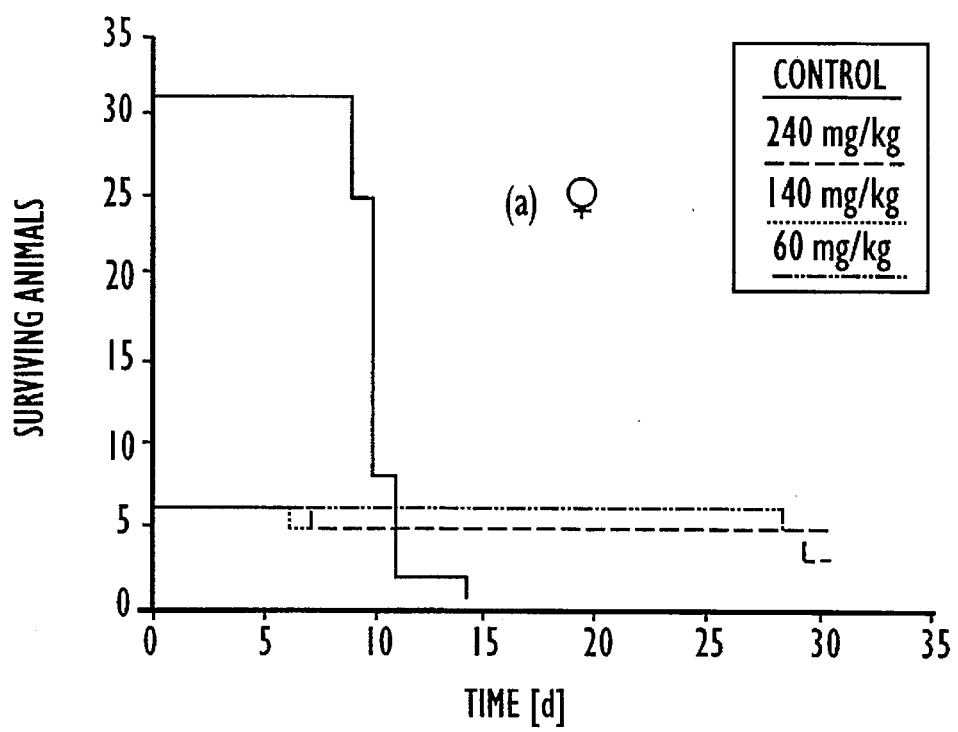
FIGS. 12a and 12b show survival times ofP388 leukemic mice treated with various doses of Glc-β-IPM.
Figure 12B:
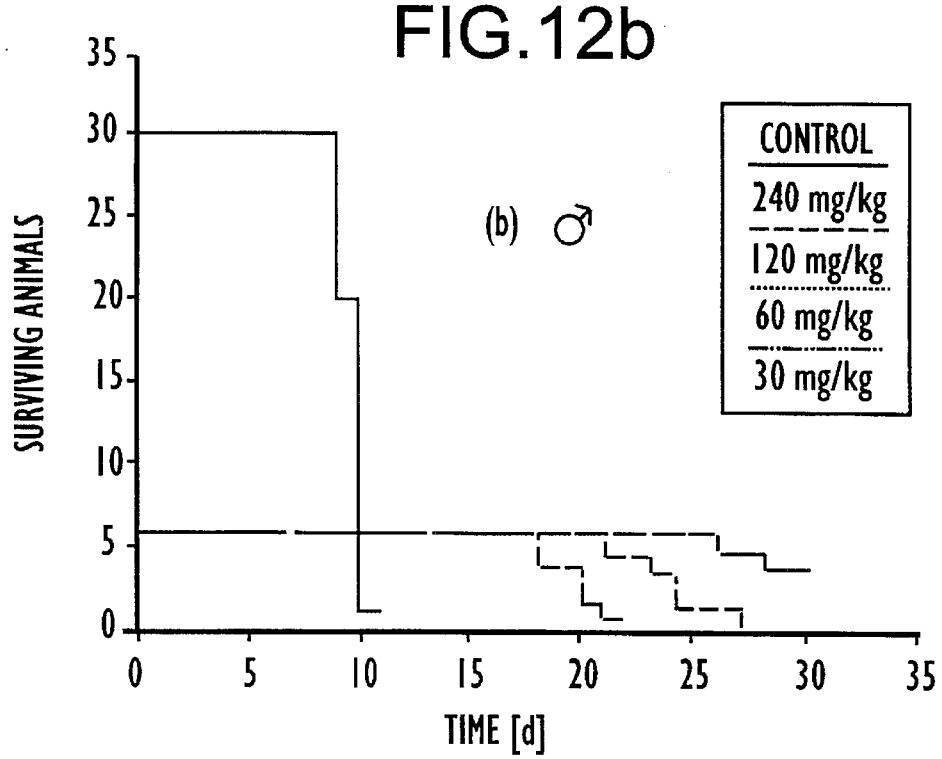
Figure 14:
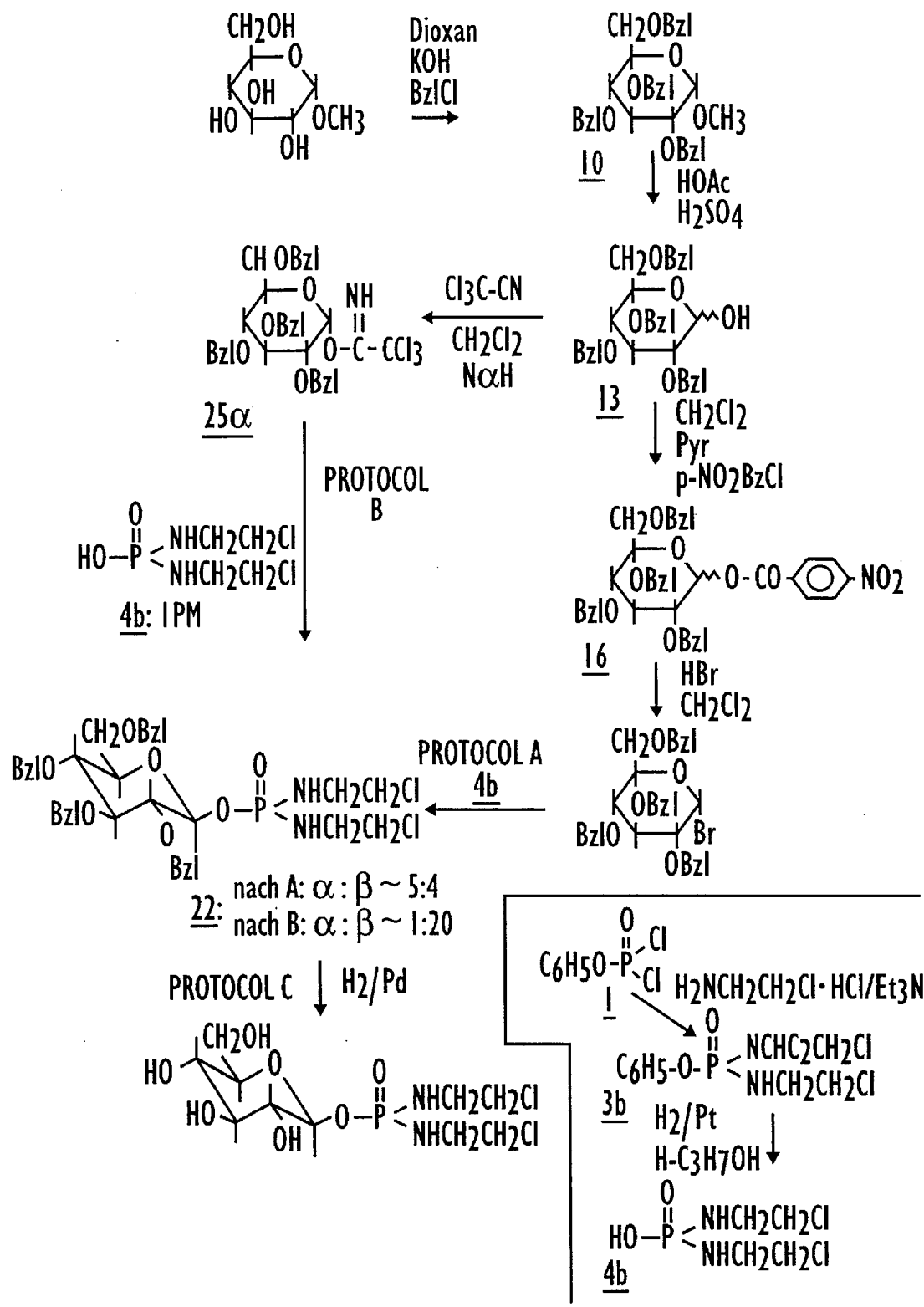
FIG. 14 shows synthetic pathways for the production of compound 28β.
Figure 15:
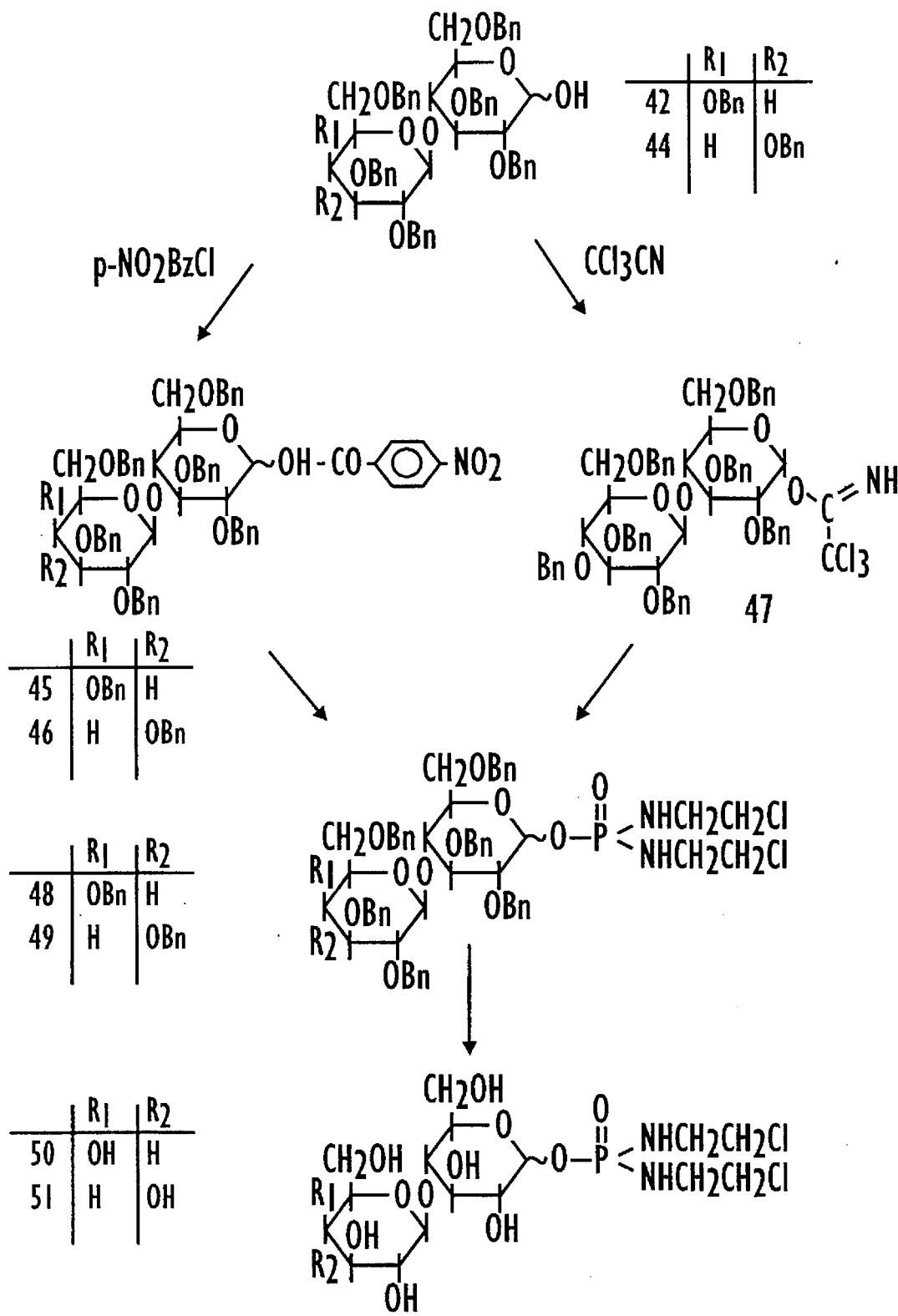
FIG. 15 shows synthetic pathways for the production of compounds 50 and 51.

In the construction of disaccharide-coupled IPM conjugates the use naturally occurring disaccharides, such as lactose or cellobiose, as the starting material, as opposed to constructing the conjugate from mono-sugar, has the advantage that the glucosidic bond between the sugars is already there, and thereby one step of stereoselective synthesis can be saved. Thus, the synthesis protocols described above are also used for the preparation of disaccharide-coupled IPM conjugates. First, a benzyl-protected disaccharide was necessary, the 1-O-position of which could be activated either with hydrogen bromide or with trichloroacetonitrile. In this way, based on the method of S. Koto (Koto et al., 1982, Nihon-Kagakkai: Nihon-Kagaku-Kaishi (J. Chem. Soc. Jpn.) 10: 1651), the disaccharide components 2,3,6,-2',3',4',6'-hepta-O-benzyl lactose and the isomeric cellobiose derivative 44 were synthesized (FIG. 7).

On incubation of the glycosides in HEPES or water with corresponding glycosidases a rapid cleavage of the glycosidic bond could be observed.

The conjugates Lac-IPM 50 and Cel-IPM 51, proved stable at room temperature in methanolic solution, just as the monosaccharide conjugates 28–30 (TLC analysis). Because each in 50 and 51 two glycosidic bonds are present, showing the same (51β) or a different configuration (f.i. 50α), along with single glucosidases enzyme mixtures were used to check the enzymatic release of IPM. The enzymatic cieavage of the pure anomeric conjugates 50 and 51 was monitored by TLC; intact conjugates or the cleavage products 28α, 28β or IPM were detected with NBP.

All conjugates were rapidly cleaved by suitable glycosidases and can release f.i. the metabolite of the general formula 1, and 1a, resp..

In the case of the disaccharide conjugates 50 and 51α cleavage of two different glycosidic bonds was required for the release of IPM. Only 52β, showing two bonds with the same configuration, could be completely cleaved by a single enzyme, β-glucosidase.

This was confirmed by measuring the biological efficiency, namely the cytotoxic activity in vitro by studies done on a murine retrothelial sarcoma, and on rat mammary tumor cell lines, and on Eb/Esb cell lines.

In vivo studies were done with the P388 leukemia in the mouse and the rat 1C32 tumor. Results of the in vitro and in vivo studies are found in FIG. 8 to 13.

Determination of toxicity showed that upon application of 100 and 1000 mg/kg Glc-β-IPM i.p. to male $CD_2F_1$ mice no acute toxicity could be observed. Autopsy of the animals after 28 days gave no findings. Also the BD6 rats with transplanted 1C32 tumor, treated with Gal-IPM (5-122.5 and 5-245 mg/kg, resp.) did not show any toxicity. The result of autopsy (among others liver, kidneys, spleen, brain, bone marrow) on day 15 after the onset of treatment gave no finding.

Summarizing, it can be stated that in vitro studies on a retrothelial sarcoma demonstrate the cytotoxicity of Aglyca-PM and -IPM, as well as the monosaccharide-IPM conjugate according to the general formula 1 and 1a, resp., and of the disaccharide conjugates acc. to the general formula 1 and 1a, resp.. In in vitro studies certain gradations become evident with the mammary tumor cell-lines 1C29, 1C32, and 1C39, because Gal-β-IPM is always the most effective agent. In vivo studies, too, showed a good effectiveness in the P388 model and with the solid 1C32 mammary tumor, and without acute toxicity. As also bone-marrow toxicity, studied in Glc-β-IPM as an example, is very low, an important requirement in the development of new anti-neoplastically active chemotherapeutic agents is fulfilled.

The following examples illustrate in detail the preparation of various, exemplary compounds.

EXAMPLE 1

General protocol for the preparation of the benzyl-protected glycosyl-phosphoric acid diamides Protocol A: Activation with hydrogenbromide 4.35 mmol of p-nitrobenzylglycose, protected in a known manner, (f.i. 3.0 g of 16), and of the N-phenyl carbamoyl derivative 17, resp., after drying over $P_2O_5$ were dissolved in 10 ml absol. $CH_2Cl_2$ (three-necked flask). At −20° C. 30 ml of a $CH_2Cl_2$ solution saturated with HBr were slowly injected under dry nitrogen. After a few seconds p-nitrobenzoic acid precipitates. After heating to r.t. (room temperature) (within 30 min.) stirring was continued for 1 h at r.t., and thereafter the reaction mixture was filtered with suction through a inverting frit into a second three-necked flask. Following evaporation of $CH_2Cl_2$ (stirring with a magnetic stirrer, water jet vacuum, waterbath, r.t.), twice 5 ml diethyl ether were added and each time evaporated as described above to remove remaining HBr. The resulting yellow to orange-colored oil was now dissolved in 20 ml $CH_2Cl_2$, and 1.0 g 4a or 4b or 54 (4.6 mmoles), and 0.85 ml triethylamine (6 mmoles) were added. After stirring for 3 d at r.t. the reaction mixture was filtered, washed twice with little water, and the organic phase was dried over $Na_2SO_4$ and rotation-evaporated. Subsequently, column chromatography of the mostly yellow, highly viscous oils was performed, and the respective anomer was found enriched in early, and late fractions, resp.. In all cases, perfect purity of anomeres could be achieved by preparative HPLC, sometimes also by crystallization.

All working steps were performed under dry nitrogen, using dried solvents, and in the dark.

Protocol B: Reaction of the phosphoric acid diamides with glycosylimidates 1.0 mmole glycosylimidate (f.i. 25) was dissolved in 20 ml acetonitrile. After the addition of 1.0 mmole phosphoric acid diamide there was stirred for 6 h under reflux (in the dark). Following filtration and rotation-evaporation chromatography on silica was performed in a known manner.

Protocol C: Cleavage of protective benzyl groups 0.1 mmole of the benzyl-protected monosaccharide derivatives 22, 23, 24, or 55, and the disaccharide conjugates 48 or 49 were dissolved in 15 ml MeOH. Following addition of appr. 5 mg Pd/activated charcoal (oxidized form, containing 10% Pd) per 0.1 megu benzyl groups to be cleaved off (that is f.i. 20 mg catalyst per 0.1 mmole 22, 35 mg per 0.1 mmole 48) hydrogenation was performed at r.t. until the cleavage of all protective groups could be demonstrated by TLC analysis (after 1–4 h). If hydrogenation was terminated immediately, the de-protected product was obtained pure after filtration and rotation-evaporation of the solution. With unnecessarily long reaction time the de-protected glycoside decomposed, and IPM 4b formed. In this case, the desired product could be recovered after TLC chromatography (silica, $CH_3CN:MeOH=70:30$).

TLC Silica, $CH_3CN:MeOH=30:70$, $R_f$ (28α)=0.58, $R_f$(4b)=0.18;
Silica, $CH_3CN:MeOH:H_2O=75:20:5$
RF-Values: 0.44 (28α), 0.48 (28β)
0.43 (29α), 0.45 (29β)
0.43 (30α), 0.41 (30β)
0.29 (50 and 51), 0.13 (4b)

For detection plates were sprayed with NBP reagent (2.5%, in acetone), heated to 120° C. for 10 min., and, after cooling to r.t., sprayed with 0.5 M NaOH. The IPM conjugates were colored deep-blue, while IPM itself was light blue.

Phosphoric acid amide mustard and ifosfamide mustard were prepared according to protocols known from the literature.

Monosaccharide-PM/IPM conjugates (analogous to 6)

Batch: 0.55 g 4a (2.5 mmoles) (N,N-di-(2-chloroethyl) phosphoric acid diamide) 1.03 g ABG (2.5 mmoles)

Yield: 30 mg as yellow, clear oil (2.2% of expected), mixture of diastereomeres (A+B, see NMR spectra)

| | | Analysis: | | |
|---|---|---|---|---|
| | | C | H | N |
| $C_{18}H_{29}Cl_2N_2O_{11}P$ | exp. | 39.24 | 5.30 | 5.08 |
| (551.3) | obs. | 39.53 | 5.38 | 4.94 | with $D_2O$, -$NH_2$), 3.35–3.70 (m, 8H, 2x -$CH_2CH_2Cl$) 3.82 (m, 1H, H-5) 4.148 (dd, H-6a(A), $J_{5,6a}$=5.0 Hz, $J_{6a,6b}$=12.5 Hz), 4.208 (dd, H-6a(B), $J_{5,6a}$=4.9 Hz, $J_{6a,6b}$=12.5 Hz), 4.244 (dd, H-6b(A), $J_{5,6b}$=2.1 Hz, $J_{6a,6b}$=12.5 Hz), 4.288 (dd, H-6b(B), $J_{5,6b}$=2.1 Hz, $J_{6a,6b}$=12.5 Hz). 5.02–5.12 (m, 2H), 5.21 and 5.23 (2t, together 1H, (B+A), J=9.5 Hz), 5.298 and 5.316 (2t, together 1H, H-1(A) und H-1(B), $J_{1,2}$=$J_{1,P}$= 7.8 Hz).

MS: m/e=331 (M-PM)

2,3,4,6-Tetra-O-acetyl β-D-glucopyranosyl N,N'-di-(2-chloroethyl)-phosphoric acid diamide 6.

To a mixture of 1.1 g 4b (5 mmoles) and 2.05 g acetobromoglucose (5 mmoles) in 50 ml dry acetone 0.5 g triethylamine (5 mmoles) were added dropwise. The reaction mixture was stirred for 48 h at r.t. in the dark. After filtration and rotation-evaporation the residue was dispersed in $CH_2Cl_2$, washed with little 0.1 M HCl, saturated $NaHCO_3$ solution, and water, dried over $Na_2SO_4$, and chromatographed on silica (acetone:n-hexane=40:60). 80 mg 6 were obtained as a clear, colorless oil which crystallized after months at 4° C.

M.p.: 91° C.
TLC: silica, acetone:n-hexane=1:1, $R_f$=0.13

| | | Analysis: | | | |
|---|---|---|---|---|---|
| | | C | H | N | Cl |
| $C_{18}H_{29}Cl_2N_2O_{11}P$ | exp. | 39.24 | 5.30 | 5.08 | 12.87 |
| (551.3) | obs. | 39.42 | 5.40 | 4.80 | 12.58 |

Penta-o-pivaloyl β-D-glucose 7
(acc. to Kund and Harreus, 1982, Liebig's Ann. Chem. 41)

Batch: 29 g D-glucose (0.16 moles) 121.2 pivaloyl chloride (1.0 mole) 200 ml chloroform, 120 ml pyridine
Yield: 66 g 7 (69% of theory)
M.p.: 154° C. (Lit.: 156°–158° C.)

| | | Analysis: | |
|---|---|---|---|
| | | C | H |
| $C_{31}H_{52}O_{11}$ | exp. | 61.98 | 8.72 |
| (600.8) | obs. | 62.16 | 8.79 |

2,3,4,6-Tetra-O-pivaloyl α-D-glucopyranosyl bromide 8
(acc. to Kund and Harreus, 1982, Liebigp's Ann. Chem. 41)

Batch: 12 g 7 (20 mmoles) 20 ml HBr in glacial acetic acid (33%) 20 ml $CH_2$, $Cl_2$
Yield: 6.4 g (55.5% of theory)
M.p.: 142° C.

| | | Analysis: | |
|---|---|---|---|
| | | C | H |
| $C_{26}H_{43}BrO_9$ | exp. | 53.89 | 7.48 |
| (579.5) | obs. | 54.24 | 7.94 |

$J_{2,3}$=9.5 Hz), 5.21 and 5.64 (2t, 2H, J=9.5 Hz, H-4 and H-3), 66.2 (d, 1H, H-1, $J_{1,2}$=4.2 Hz).

2,3,4,6-Tetra-O-pivaloyl β-D-glucopyranosyl N,N'-di-(2-(chloroethyl) phosphoric acid diamide 9

To a mixture of 0.38 g 4b (1.725 mmoles) and 1.0 g 8 (1.725 mmoles) in 50 ml acetone 0.5 g $Ag_2CO_3$ (1.8 mmoles) were added at r.t.. After stirring for 24 h (in the dark) at r.t., the reaction mixture was filtered, concentrated, and chromatographed over silica (acetone:n-hexane=25:75). 160 mg 9 (12.9% of theory) were obtained as a clear, colorless oil which crystallized after months at +4° C.

M.p.: 94° C.
TLC: silica, acetone:n-hexane=1:1, $R_f$=0.43

| | | Analysis: | | | |
|---|---|---|---|---|---|
| | | C | H | N | Cl |
| $C_{30}H_{54}Cl_2N_2O_2P$ | exp. | 50.08 | 7.42 | 3.89 | 9.86 |
| (719.54) | obs. | 51.35 | 7.98 | 3.24 | 9.36 |

Methyl 2,3,4,6-tetra-O-benzyl α-D-glucopyranoside 10
(acc. to Methods in Carbohydrate Chemistry, 1972)

Batch: 50 g methyl α-D-glucopyranoside (257 mmoles) 250 g KOH (powdered) 150 ml dioxane 318 ml benzylchloride (2.76 moles)

Yield: 116 g 10 (81.3% of theory) as highly-viscous, yellow, clear oil

| Analysis: | | | |
|---|---|---|---|
| | | C | H |
| $C_{35}H_{38}O_6$ (554.68) | exp. obs. | 75.79 76.19 | 6.91 6.93 |

Methyl 2,3,4,6-tetra-O-benzyl α-D-galactopyranoside 11 (analogous to 10)

Batch: 40 g methyl α-D-galactopyranoside (206 mmoles) 200 g KOH (powdered) 200 ml dioxane 280 ml benzylchloride Yield: 102 g 11 (89.3% of theory) as yellow, clear oil

| Analysis: | | | |
|---|---|---|---|
| | | C | H |
| $C_{35}H_{38}O_6$ (554.68) | exp. obs. | 75.79 76.07 | 6.91 6.67 |

· Methyl 2,3,4,6-tetra-O-benzyl α-D-mannopyranoside 12 (acc. to Koto et al., 1976)

Batch: 18 g methyl α-D-mannopyranoside (92.7 mmoles) 81 g NaH suspension (20%) 450 ml benzylchloride Raw yield: After the washing process 2 phases form. After removing the upper, colorless phase (white oil), 52 g yellow, slightly turbid oil were obtained which could be reacted to 15 without further purification. Part of the oil was chromatographed (silica, EE:PE =40:60): yellow, clear oil -$^1$H-NMR: 90 MHz, $CDCl_3$ =3.31 (s, 3H, -OMe), 3.65–4.15 (m, 6H, sugar protons), 4.43–5.10 (m, 9H, H-1 und 4x-$CH_2$-Ph), 7.1–7.45 (m, 2OH, 4x-Ph).

2,3,4,6-Tetra-O-benzyl α-D-glucopyranose 13 (acc. to Methods in Carbohydrate Chemistry, 1982)

Batch: 115 g 10 (207 mmoles)

Yield: 54 g 13 (48.3% of theory)

M.p.: 152° C. (recrystallized from methanol)

| Analysis: | | | |
|---|---|---|---|
| | | C | H |
| $C_{34}H_{36}O_6$ (540.66) | exp. obs. | 75.53 75.69 | 6.71 6.91 |

2,3,4,6-Tetra-O-benzyl α-D-galactopyranose 14 (acc. to Kronzer and Schuerch, 1974, Carboh. Res. 33: 273)

Batch: 30 g 11 (54 mmoles) 500 ml acetic acid (80%) 150 ml 1 N HCl

Yield: 9.8;6 g 14 (98% of theory), yellow, clear oil $^1$H-NMR: 90 MHz, $CDCl_3$ δ=3.47 (d, 1H, exchangeable with $D_2O$, -OH), 3.5–4.3 (m, 6H, sugar protons.), 4.35–5.05 (m, 8H, 4x-$CH_2$-Ph), 5.28 (dd, 1H, H-1, $J_{1,2}$=3.2 Hz), 7.1–7.5 (m, 2OH, 4x-Ph).

2,3,4,6-Tetra-O-benzyl D-mannopyranose 15

50 g of the mixture 12 (appr. 90 mmoles, still contains some white oil) were dissolved in 800 ml glacial acetic acid and heated to 80°–85° C. 120 ml 2 N HCl were added dropwise within 60 min.; after further 90 min. 200 ml water were added, the reaction mixture was cooled to r.t., and subsequently extracted with 3 200 ml toluene. The organic phase was washed with sat. $NaHCO_3$ solution and water, dried over $Na_2SO_4$, and concentrated by rotation-evaporation. The resulting brown syrup was chromanographed (silica, EE:EP=30:70) and 32.2 g 15 (68.3% of theory) were obtained as a yellow oil.

$^1$H-NMR: 90 MHz, $CDCl_3$ δ=3.5–4.3 (m, 7H, 1H exchangeable with $D_2O$, -OH and 6 sugar protons, 4.35–5.05 (m, 8H, 4x-$CH_2$-Ph), 5.22 (d, 1H, H-1, $J_{1,2}$-2Hz), 7.05–7.4 (m, 2OH 4x-Ph).

2,3,4,6-Tetra-O-benzyl 1-O-p-nitrobenzoyl D-glucopyranoside 16 (acc. to Methods in Carbohydrate Chemistry, 1972)

Batch: 15.5 g 13 (28.7 mmoles) 6 g p-nitrobenzoyl chloride (32.3 mmoles) 3.75 ml pyridine Yield: 15.6 g 16 (78.8% of theory) as white powder M.p.: 93°–98° C. (from ethanol)

Recrystallization from diisopropylether gave 16α as needles.

M.p.: 122° C.

| Analysis: | | | | |
|---|---|---|---|---|
| | | C | H | N |
| $C_{41}H_{39}NO_9$ (689.76) | exp. obs. | 71.39 71.37 | 5.70 5.67 | 2.03 2.04 |

From the mother liquor 16β crystallized, m.p. 98° C.

203,4,6-Tetra-O-benzyl 1-O-(N-phenylcarbamoyl) D-galactopyranose 17 (acc. to Kronzer and Schuerch, 1974, Carboh. Res. 33: 273)

Batch: 18.7 g 14 (34.6 mmoles) 50 ml pyridine 5.4 ml phenylisocyanate

Yield: 8.0 g 17 (35% of theory), (α:β=35:65)

M.p.: 120°–122° C. (from ethanol)

| Analysis: | | | | |
|---|---|---|---|---|
| | | C | H | N |
| $C_{41}H_{41}NO_7$ (659.78) | exp. obs. | 74.64 74.21 | 6.26 5.97 | 2.12 2.36 |

From the mother liquor 17α crystallizes, m.p. 143° C;

2,3,4,6-Tetra-O-benzyl 1-O-p-nitrobenzoyl α-D-mannopyranoside 18 (acc. to Ko,to et al., 1976, Bull. Chem. Soc. Jpn. 49: 2639)

Batch: 9.8 g 15 (18.1 mmoles) 4.9 g p-nitrobenzoyl chloride 50 ml pyridine

Yield: after flash chromatography (silica 60, EE:PE= 25:75) 7.7 g 18 (61.7% of theory) crystallized from diisopropyl ether M.p.: 105° C.

| Analysis: | | | | |
|---|---|---|---|---|
| | | C | H | N |
| $C_{41}H_{39}NO_9$ (689.76) | exp. obs. | 71.39 71.46 | 5.70 5.58 | 2.03 1.90 |

2,3,4,6-Tetra-O-benzyl N,N'-di-(2-chloroethyl) phosphoric acid diamide 22

1. acc. to protocol A

Batch: 3.0 g 16(4.35 mmoles)

Yield: after column chromatography (silica, EE:PE= 60:40) 2.2 g 22 (68% of theory), mixture of anomers: α:β=5:4 ($^1$H-NMR).

TLC: Silica EE:PE=60:40 $R_f$=0.28, $R_f$ (α)>$R_f$ (β)

HPLC (anal.): Silica, EE:hexane=75:25, flow: 1.0 ml/min. $R_t$ (α)=12.53', $R_t$ (β)=14.04';

HPLC (prep.): Silica, EE:hexane:MeOH=58:42:0.5, flow: 10.0 ml/min $R_t$ (α)=45', $R_t$ (β)=55';

| | | Analysis: | | | | |
|---|---|---|---|---|---|---|
| | | C | H | N | Cl | |
| $C_{38}H_{45}Cl_2N_2O_7P$ | exp. | 61.38 | 6.10 | 3.77 | 9.54 | |
| (743.60) | obs. | 61.15 | 6.22 | 3.78 | 9.61 | 22α |
| | obs. | 60.82 | 6.29 | 3.61 | 9.37 | 22β |

2. acc. to protocol B

Batch: 4.5 g 25α (6.75 mmoles) 1.45 g 4b (6.57 mmoles)

Yield: after column chromatography (see above): 2.06 g 22 (42.2% of theory), anomeric ratio α:β appr. 1:20 (acc. to $^1$H-NMR and HPLC)

Batch: 50 mg 25β (0.073 mmoles) 16.1 mg 4b (0.073 mmoles)

TLC shows product with $R_f$=0.28 and little tetrabenzyl glucose 13, as well as some starting material 25β, anomeric ratio α:β=1.1 (HPLC)

2,3,4,6-Tetra-O-benzyl D-galactopyranosyl N,N'-di-(2-chloroethyl) phosphoric acid diamide 23

1. acc. to protocol A

Batch: 2.6 g 17 (3.94 mmoes) 0.9 g 4b (4.07 mmoles)

Yield: after column chromatography (silica, EE:PE= 60:40): 1.9 g 23 (65% of theory), mixture anomers α:β=1:1 ($^1$H-NMR)

TLC: Silica, EE:PE=60:40, $R_f$=0.27, $R_f$ (α)>$R_f$ (β)

HPLC (anal.): Silica, EE:hexane=75:25, flow: 1.0 ml/min: $R_t$ (α)=14.26', $R_t$ (β)=18.03';

HPLC (prep.): Silica, EE:hexane:MeOH=58:42:0.5, $R_t$ (α)=51', $R_t$ (β)=62';

| | | Analysis: | | | | |
|---|---|---|---|---|---|---|
| | | C | H | N | Cl | |
| $C_{38}H_{45}Cl_2N_2O_7P$ | exp. | 61.38 | 6.10 | 3.77 | 9.54 | |
| (743.60) | obs. | 61.26 | 6.19 | 3.76 | 9.76 | 23α |
| | obs. | 61.16 | 6.26 | 3.76 | 9.66 | 23β |

2. acc. to protocol B

Batch: 685 mg 26α (1.0 mmole) 221 mg 4b (1.0 mmole)

Yield: in the filtered reaction mixture the ratio of anomers α:β was 55:45 (HPLC). After TLC (see above) 260 mg 23 (38% of theory) were obtained.

2,3,4,6-Tetra-O-benzyl D-mannopyranosyl N,N'-di-(2-chloroethyl) phosphoric acid diamide 24

1. acc. to protocol A

Batch: 2.3 g 18 (3.33 mmoles) 0.75 g 4b (3.39 mmoles)

Yield: after column chromatography (siliCa, EE:PE= 80:20) 1.16 g 24 (47% of theory), anomeric mixture: α:β= 55:45 ($^1$H-NMR)

TLC: Silica, EE:PE=60:40, $R_f$ (α)=0.23, $R_f$ (β)=0.19

HPLC (anal.): Silica, EE:hexane=75:25, flow: 1.0 ml/min. $R_t$ (α)=13.05', $R_t$ (β)=21.61';

HPLC (prep.): Silica, EE:hexane:MeOH=64:36:0.5, flow: 10 ml/min $R_t$ (α)=45', $R_t$ (β)=70';

| | | Analysis: | | | |
|---|---|---|---|---|---|
| | | C | H | N | |
| $C_{38}H_{45}Cl_2N_2O_7P$ | exp. | 61.38 | 6.10 | 3.77 | |
| (743.60) | obs. | 60.98 | 6.32 | 3.52 | 24α |
| | obs. | 60.98 | 6.19 | 3.29 | 24β |

2. acc. to protocol B

Batch: 3.2 g 27α (4.67 mmoles) 1.04 g 4b (4.70 mmoles)

Yield: TLC showed almost quantitative reaction to 24α with $R_f$=0.23. In the filtered reaction mixture only the α-anomer is found (HPLC). After column chromatography 1.6 g 24α (45% of theory) were obtained.

O-(2,3,4,6-Tetra-O-benzyl α-D-glucopyranosyl) trichloroacetimidate 25α

(acc. to Schmidt and Stumpp, 1983, Liebig's Ann. Chem., 1249)

Batch: 9.2 g 13 (17 mmoles) 7.7 ml trichloroacetonitrile 680 mg NaH

Yield: 10.9 g 25α (93.6% of theory), colorless, clear oil.
TLC: Silica, PE:e=1:1, $R_f$=0.44

$^1$H-NMR: 90 MHz, $CDCl_3$. δ=3.6–5.(m, 14H), 6.51 (d, 1H, H-1, $J_{1,2}$=3.5 Hz), 6.95–7.55 (m, 20H, 4x-Ph), 8.55 (s, 1H, -NH-).

O-(2,3,4,6-Tetra-O-benzyl β-D-glucopyranosyl) trichloroacetimidate 25α

(acc. to Schmidt et al., 1984, Liebig's Ann. Chem., 680)

Batch: 1.3 g 13 (2.4 mmoles) 1.25 g $K_2CO_3$ (dried) 1.25 ml trichloroacetonitrile Yield: after gel filtration on silica: slightly yellowish oil (1.6 g, 97% of theory, α:β=1:5); after TLC (silica, E:PE= 2:3) pure 25β was obtained as a colorless oil (50 mg, 30% of theory)

TLC: Silica, PE:E=1:1, $R_f$=0.37

$^1$H-NMR: 90 MHz, $CDCl_3$ δ=3.55–3.90 (m, 6H), 4.40–5.05 (m, 8H), 5.82 (d, 1H, H-1), 7.1–7.5 (m, 20H, 4x-Ph), 8.70 (s, 1H, -NH-).

O-(2,3,4,6-Tetra-O-benzyl D-galactopyranosyl) trochloroacetimidate 26

(acc. to Schmidt et al., 1984, Liebig's Ann. Chem., 1343)

Batch: 1.5 g 14 (2.77 mmoles) 1.4 ml trichloroacetonitrile 80 mg NaH

Yield: after gel filtration on silica an anomeric ratio of α:β of 4:1 was determined ($^1$H-NMR: 90 MHz, $CDCl_3$, Nr. H14208, δ=5.72 (d, 0.2H, H-1 (β), $J_{1,2}$=8.0 Hz), 6.52 (d, 0.8 H, H-1 (α), $J_{1,2}$=3.7 Hz), 8.51 (s, 0.8H, -NH- (α) exchangeable with $D_2O$), 8.60 (s, 0.2H, - NH-(β), exchangeable with $D_2O$).

After column chromatography (silica, E:PE =1:1) 2 fractions were obtained:

F1: 1130 mg 26α (59.5% of theory) as colorless oil, $^1$H-NHR: 500 MHz, $CDCl_3$, Nr. H14112

F2: 320 mg 26 (16.8% of theory) as yellowish oil (α:β= 2:1) $^1$H-NMR: 500 MHz, $CDCl_3$, Nr. H14113

TLC: Silica, PE:E =1:1, $R_f$ (α)=0.43, $R_f$ (β)=0.34

O-(2,3,4,6-Tetra-O-benzyl α-D-mannopyranosyl) trichloroacetimidate 27α

(acc. to Schmidt et al., 1984, Liebig's Ann. Chem., 1343)

Batch: 4.5 g 15 (8.27 mmoles) 4 ml trichloroacetonitrile 45 mg NaH

Yield: after column chromatography: 4.45 g 27α (65% of theory) as colorless oil

TLC: Silica, E:PE=3:2, $R_f$=0.51

¹H-NMR: 90 MHz, CDCl₃ δ=3.65–5.0 (m, 14H), 6.33 (d, 1H, H-1, $J_{1,2}$≈1.5 Hz), 7.05–7.5 (m, 20H, 4x-Ph), 8.52 (s, 1H, -NH-).

α-D-Glucopyranosyl N,N'-di-(2-chloroethyl) phosphoric acid diamide 28α

Hydrogenation of 22α acc. to protocol C

¹H-NMR: 500 MHz, D₂O, Nr. 13943 δ=3.25–3.32 (m, 4H, 2x-CH₂-), 3.488 (t, 1H, J=9.5 Hz), 3.61–3.67 (m, 5H with 2x-CH₂), 3.719 (t, 1H, J≈9.5 Hz), 3.75–3.90 (m, 3H), 5.605 (dd, 1H, H-1, $J_{1,2}$=3.4 Hz, $J_{1,P}$=7.8 Hz).

| FAB-MS: | Nr. MSN 13608 | | | |
|---|---|---|---|---|
| | positive: | m/e = | 383, 385, 387 | (M+H)⁺ |
| | | | 221, 223, 225 | (IPM+H)⁺ |

β-D-Glucopyranosyl N,N'-di-(2-chloroethyl) phosphoric acid diamide 28β

Hydrogenation of 2β acc. to protocol C

| | Analysis: | | | |
|---|---|---|---|---|
| | | C | H | N |
| C₁₀H₂₁Cl₂N₂O₇P | exp. | 31.35 | 5.53 | 7.31 |
| (383.10) | obs. | 31.03 | 5.04 | 6.82 |

α-D-Galactopyranosyl N,N'-di-(2-chloroethyl) phosphoric acid diamide 29α

Hydrogenation of 23α acc. to protocol C

¹H-NMR: 500 MHz, D₂O, Nr. 13945 δ=3.26–3.32 (m, 4H, 2x-CH₂-), 3.635–3.665 (m, 4H, 2-CH₂-), 3.74–4.05 (m, 5H), 4.098 (m, 1H), 5.642 (dd, 1H, H-1, $J_{1,2}$=3.1 Hz, $J_{1,P}$=7.8 Hz).

| FAB-MS: | Nr. MSN 13612 | | | |
|---|---|---|---|---|
| | positive | m/e = | 383 | (M+H)⁺ |
| | | | 221, 223, 225 | (IPM+H)⁺ |
| | negative | m/e = | 381, 383, 385 | (M–H)⁻ |
| | | | 219, 221, 223 | (IPM–H)⁻ |

β-D-Galactopyranosyl N,N'-di-(2-chloroethyl) phosphoric acid diamide 29β

Hydrogenation of 23β acc. to protocol C

¹H-NMR: 500 MHz, D₂O, Nr. 13946 δ=3.26–3.32 (m, 4H, 2x -CH₂-), 3.605 (d, 1H), 3.63–3.67 (m, 4H, 2x -CH₂-), 3.692 (dd, 1H, J=3.5 und J=10.0 Hz), 3.70–3.95 (m, 4H), 4.950 (t, 1H, H-1, $J_{1,2}$=J=8.0 Hz).

| FAB-MS: | Nr. MSN 13613 | | | |
|---|---|---|---|---|
| | negative | m/e = | 381, 383, 385 | (M–H)⁻ |
| | | | 219, 221, 223 | (IPM–H)⁻ |

α-D-Mannopyranosyl N,N'-di-(2-chloroethyl) phosphoric acid diamide 30α

Hydrogenation of 24α acc. to protocol C

¹H-NMR 500 MHz, D₂O , Nr. 13947 δ=3.26–3.32 (m, 4H, 2x -CH₂-), 3.5–4.0 (m, 9H with 4H at 3.63–3.67, 2x-CH₂-), 4.018 (dd, 1H), 5.564 (dd, 1H, H-1, J=$_{1,2}$=2.0 Hz, $J_{1,P}$=8.0 Hz).

| FAB-MS: | Nr. 13614 | | | |
|---|---|---|---|---|
| | negative | m/e = | 381, 383, 385 | (M–H)⁻ |
| | | | 219, 221, 223 | (IPM–H)⁻ |

β-D-Mannopyranosyl N, N'-di-(2-chloroethyl) phosphoric acid diamide 30β

Hydrogenation of 24β acc. to protocol C

¹H-NMR: 500 MHz, D₂O, Nr. 13948 δ=3.26–3.33 (m, 4H, 2x -CH₂-), 3.45 (m, 1H, H-5), 3.604 (t, 1H, H-4, J3,4=$J_{4,5}$=9.8 Hz), 3.63–3.67 (m, 4H, 2x -CH₂-), 3.703 (dd, 1H, H-3, $J_{2,3}$=3.2 Hz, $J_{3,4}$=9.8 Hz), 3.754 (dd, 1H, H-6a, $J_{5,6a}$=6.2 Hz, $J_{6a,6b}$≈12.5 Hz), 3.931 (dd, 1H, H-6b, $J_{5,6b}$=2.1 Hz, $J_{6a,6b}$≈12.5 Hz), 4.052 (dd, 1H, H-2, $J_{1,2}$≈1.1 Hz, $J_{2,3}$=3.2 Hz), 5.282 (dd, 1H, H-1, $J_{1,2}$≈1.1 Hz, $J_{1,P}$=8,6 Hz).

| FAB-MS: | Nr. 13615 | | | |
|---|---|---|---|---|
| | negative | m/e = | 331, 383, 385 | (M–H)⁻ |
| | | | 219, 221, 223 | (IPM–H)⁻ |

Di-(2-chloroethyl) phosphoric acid diamide dichloride 33 (acc. to Friedman and Seligman, 1954, J. Am. Chem. Soc. 76: 655)

Batch: 130 ml POCl₃ (1.4 mole) 50 g Bis-(2-chloroethyl) amine hydrochloride

Yield: 53 g 33 as white crystals

M.p.: 54° C. (from acetone/PE)

| | Analysis: | | | | |
|---|---|---|---|---|---|
| | | C | H | N | Cl |
| C₄H₈Cl₄NOP | exp. | 18.56 | 3.11 | 5.41 | 54.77 |
| (258.9) | obs. | 18.67 | 3.13 | 5.35 | 54.90 |

EXAMPLE 2

Disaccharide-IPM conjugates

Octa-O-acetyl lactose 35.

A mixture of 100 g lactose (147 mmoles), 400 ml acetanhydride, and 25 g water-free sodium acetate was stirred at 120°–135° C. for 60 min. After cooling it was poured on ice-water and extracted with CH₂Cl₂. The organic phase was washed neutral with sat. NaHCO₃ and H₂O, dried over Na₂SO₄, and concentrated by rotation-evaporation. Crystallization from ethanol yielded 153 g 35 (80% of theory).

M.p.: 79°–92° C.

TLC: Silica, Toluene:2-butanone=10:4, $R_f$=0.43

| | Analysis: | | |
|---|---|---|---|
| | | C | H |
| C₂₈H₃₀O₁₉ | exp. | 49.56 | 5.64 |
| (678.6) | obs. | 49.37 | 5.80 |

Allyl-4-O-(2,3,4,6-tetra-O-acetyl β-D-galactopyranosyl) 2,3,6-tri-O-acetyl D-glucopyranoside 37 (acc. to Koto et al., 1982, J. Chem. Soc. Jpn. 10: 1651)

34 g (50 mmoles) 35 were dissolved in 60 ml CHCl₃. At 0° C. 20.6 ml acetylbromide (276 mmoles) and 4.56 ml H₂O were added. After stirring for 2.5 h at r.t. the yellow, clear solution was concentrated by rotation-evaporation, and a yellow foam (hepta-O-acetyl α-D-lactosylbromide) was obtained with:

¹H-NMR: 90 MHz, CDCl₃ δ=1.95–2.20 (m, 21H, 7x-OAc), 3.7–5.65 (m, 13H. sugar protons), 6.51 (d, 1H, H-1, $J_{1,2}$=4 Hz).

The foam was dissolved in 400 ml allyl alcohol at 35° C. After addition of 30 g silver carbonate the mixture was stirred for 1 d at r.t. (in the dark, followed by filtration and concentration by rotation-evaporation. The residue was dispersed in ether and, after another filtration and concentration step chromatographed on silic 60 (toluene:2-butanone= 10:1→10:3). 18.2 g 37(53.8% of theory) were obtained as a clear oil.

TLC: Silica, toluene:2-butanone=10:4 (10:1), $R_f$=0.47 (0.08)

| | Analysis: | | |
|---|---|---|---|
| | | C | H |
| $C_{29}H_{40}O_{18}$ | exp. | 51.48 | 5.96 |
| (676.62) | obs. | 51.44 | 5.92 |

Allyl-4-O-(2,3,4,6-tetra-O-acetyl β-D-glucopyranosyl) 2,3,6-tri-O-acetyl D-glucopyranoside 38

(analogous to 37.)

Batch: 29 g α-D-cellobiose octaacetate (42.6 mmoles) (Ega-Chemie) 17.6 ml acetylbromide 3.9 ml $H_2O$ Intermediate product: hepta-O-acetyl α-D-cellobiosylbromide ¹H-NMR: 90 MHz, CDCl₃ δ=6.51 (d, 1H, H-1, $J_{1,2}$=4 Hz)

Yield: After column chromatography (silica, EE:PE) and crystallization from diisopropyl ether 16.5 g 38 (57% of theory) were obtained.

M.p.: 179° C.

TLC: Silica, toluene:2-butanone=10:4, $R_f$=0.49;

| | Analysis: | | |
|---|---|---|---|
| | | C | H |
| $C_{29}H_{40}O_{18}$ | exp. | 51.48 | 5.96 |
| (679.62) | obs. | 51.45 | 6.07 |

Allyl-4-O-(2,3,4,6-tetra-O-benzyl β-D-galactopyranosyl) 2,3,6-tri-O-benzyl D-glucopyranoside 39

(acc to Koto et al 1982 J Chem. Soc. Jpn. 10: 1651=

Batch: 19.5 g 37 (28.8 mmoles) 800 ml benzylchloride 105 g KOH, powdered

Yield: after column chromatography (silica, toluene:2-butanone =100:1→10:1, and crystallization from EE/hexane 21.3 g 39, (73% of theory) were obtained as needles.

TLC: Silica, toluene:2-butanone=10:1, $R_f$=0.50
M.p.: 73° C.

| | Analysis: | | |
|---|---|---|---|
| | | C | H |
| $C_{64}H_{68}O_{11}$ | exp. | 75.87 | 6.76 |
| (1013.24) | obs. | 75.66 | 6.63 |

Allyl4-O-(2,3,4,6-tetra-O-benzyl β-D-glucopyranosyl) 2,3,6-tri-O-benzyl D-glucopyranoside 40

(analogous to 39)

Batch: 2.65 g 38 (3.92 mmoles) 100 ml benzylchloride 14.3 g KOH, powdered

Yield: after column chromatography and crystallisation from diisopropyl ether/hexane 2.82 g 40. (71% of theory) were obtained.

TLC: Silica, toluene:2-butanone=10:1, $R_f$=0.50
M.p.: 102° C.

| | Analysis: | | |
|---|---|---|---|
| | | C | H |
| $C_{64}H_{68}O_{11}$ | exp. | 75.87 | 6.76 |
| (1013.24) | obs. | 76.17 | 6.57 |

4-O-(2,3,4,6-Tetra-O-benzyl β-D-galactopyranosyl) 2,3,4-tri-O-benzyl D-glucopyranose 43

A) Isomerization with t-BuOK to give 1-propenyl ether 41

A mixture of 4.9 g 39 (4.84 mmoles) and 1.3 g t-BuOK in 30 ml DMSO was stirred for 2 h at 110° C. under nitrogen. DMSO was removed by rotation-evaporation, the residue was dissolved in a mixture of ether/water. The ether phase was isolated, the water phase was reextracted twice with ether. The combined ether phases were dried over $Na_2SO_4$ and concentrated by rotation-concentration. 4.02 g 41. (4.13 mmoles) were obtained as a brown oil (raw yield: 85%).

TLC: Silica, toluene:2-butanone=10:1, $R_f$=0.62

B) Hydrolysis of the 1-propenyl ether 41 with HgCl₂ to give 43

(acc. to Gigg and Warren, 1968, J. Chem. Soc. (C), 1903)

To a mixture of 4.02 g 41 (4.13 mmoles) and 1130 mg HgO in 10 ml acetone/water (10:1) 1150 mg $HgCl_2$ in 10 ml acetone/water (10:1) were added dropwise over 5 min. After stirring for 1 h at r.t. the reaction mixture was filtered through Celite, concentrated by rotation-evaporation, and dispersed in ether. The ether phase was washed with 10 ml of a half-saturated KJ solution, and with water. After drying over $Na_2SO_4$ and rotation-evaporation it was chromatographed over silica (toluene:2-butanone=100:1→10:5). 43 was obtained as a yellow oil which crystallized from ether/ PE: 2.6 g (55% of theory, based on 39, anomeric mixture, α:β appr. 2:1 after ¹³C-NMR).

M.p.: 103° C.

TLC: Silica, toluene:2-butanone=10:1, $R_f$=0.22

| | Analysis: | | |
|---|---|---|---|
| | | C | H |
| $C_{61}H_{64}O_{11}$ | exp. | 75.29 | 6.63 |
| (973.17) | obs. | 74.79 | 6.65 |

4-O-(2,3,4,6-Tetra-O-benzyl β-D-glucopyranosyl) 2,3,4-tri-O-benzyl D-glucopyranose 44

1. analogous to 43: Isomerization with t-BuOK to give the 1-propenyl ether 42. and subsequent hydrolysis with HgCl₂

Yield: 47.7% of theory (after column chromatography)

2. Isomerization with Tris(triphenylphosphin) rhodium chloride (RhCl(PPh₃)₃) and subsequent hydrolysis with 1 N HCl (acc. to Corey and Suggs, 1973, J. Org. Chem. 38: 3224)

125 mg 40 (0.123 mmoles) were boiled for 3 h in 30 ml EtOH/water with 2 mg diazabicyclo{2.2.2} octane (0.027 mmoles) and 12 mg RhCl(PPh₃)₃ (0.009 mmoles). Then 6 ml 1 N HCl were added and boiled for another 2 h. After cooling NaHCO₃ solution was added and extracted with ether. The organic phase was washed with water, dried over night over $Na_2SO_4$, and rotation-evaporated. After column chromatography (silica, toluene:2-butanone=100:1 →100:5) 109 mg 44 (91% of theory, based on 40, anomeric mixture, α:β appr. 3:1 after ¹³C-NMR) were obtained as a colorless oil.

TLC: Silica, toluene:2-butanone=10:1, $R_f$=0.22

$^1$H-NMR: 90 MHz, CDCl$_3$ δ=3.05 and 3.25 (2d, 1H, -OH, (α and β), exchangeable with D$_2$O), 3.3–5.2 (m, 28H), 7.1–7.5 (m, 35H, 7x-Ph).

$^{13}$C- NMR: Nr. C 14897, CDCl$_3$ δ=91.38 (s, C-1α), 97.42 (s, C-1β), 102.68 (s, C-1').

FAB-MS: Nr. 13689 (pos., Glycerin, DMLF/HCl) m/e= 973 (M+H)$^+$

4-O-(2,3,4,6-Tetra-O-benzyl β-D-galactopyranosyl 2,3,6-tri-O-benzyl 1-O-p-nitrobenzoyl D-glucopyranose 45

To 480 mg 43 (0.49 mmoles) in CH$_2$Cl$_2$ ml of a solution of 130 mg p-nitrobenzoylchloride and 0.3 ml pyridine in CH$_2$Cl$_2$ were dropwise at r.t. After stirring for 20 h at r.t. almost no starting material 43 was present in TLC (silica, toluene:2-butanone =10:1), but two products with $R_f$=0.42 and 0.49. After washing with 0.5 N HCl, 1 N NaHCO$_3$, and water, and drying over Na$_2$SO$_4$ a highly viscous oil was obtained. From ethanol 435 mg 45 (79% of theory, anomeric mixture, α:β=3:7 after $^1$H-NMR) crystallized.

M.p.: 112° C.

| Analysis: | | C | H | N |
|---|---|---|---|---|
| C$_{68}$H$_{67}$O$_{14}$N | exp. | 72.77 | 6.02 | 1.25 |
| (1122.28) | obs. | 73.05 | 6.25 | 1.11 |

4-O-(2,3,4,6-Tetra-O-benzyl β-D-glucopyranosyl 2,3,6-tri-O-benzyl 1-O-p-nitrobenzoyl D-glucopyranose 46 (analogous to 45.)

Batch: 520 mg 44 (0.534 mmoles) 150 mg p-nitrobenzoyl chloride 0.4 ml pyridine

Yield: After 20 h TLC (silica, toluene:2-butanone=10:1) showed two products with $R_f$=0.43 and 0.49, and a little starting material with $R_f$=0.22. After column chromatography (silica, toluene:2-butanone =20:1) 320 mg 46 were obtained as oil (53.4% of theory). From diisopropyl ether 46α crystallized.

M.p.: 169° C.

| Analysis: | | C | H | N |
|---|---|---|---|---|
| C$_{68}$H$_{67}$O$_{14}$N | exp. | 72.77 | 6.02 | 1.25 |
| (1122.28) | obs. | 72.70 | 6.01 | 1.07 |

O-{4-O-(2,3,4,6-Tetra-O-benzyl β-D-glucopyranosyl 2,4,6-tri-O-benzyl α-D-glucopyranosyl] trichloroacetimidate 47 (analogous to 25α)

Batch: 130 mg 4.4 (0.133 mmoles) 60 μl trichloroacetonitrile 5.3 mg NaH

Yield: after column chromatography (silica, E:PE=2:3) 120 mg 47 (80% of theory) were obtained as a clear, colorless oil.

TLC: silica, E:PE=3:2, $R_f$=0.49

$^1$H-NMR: 90 MHz, CDCl$_3$ δ=3.3–5.2 (m, 27H), 6.44 (d, 1H, H-1, J$_{1,2}$=4 Hz), 7.1–7.4 (m, 35H, 7x -Ph), 8.57 (s, 1H, -NH-,exchangeable with D$_2$O).

C$_{63}$H$_{64}$Cl$_3$NO$_{11}$ (1117.56)

4-O-(2,3,4,6-Tetra-O-benzyl β-D-galactopyranosyl) 2,3,6-tri-O-benzyl D-glucopyranosyl N, N'-di-(2-chloroethyl) phosphoric acid diamide 48 acc. to protocol A

Batch: 100 mg 45 (0.089 mmoles) 21 mg 4b (0.095 mmoles)

Yield: after column chromatography (silica, EE:PE= 40:60 →70:30) 2 fractions were obtained: F1: 7 mg 48, β>>α (6.7% of theory) F2: 40 mg 48, α>>β (38.2% of theory)

TLC: silica, EE/PE=80:20, $R_f$ (α)=0.37, $R_f$ (β)=0.42; C$_{65}$H$_{73}$Cl$_2$N$_2$O$_{12}$P (1176.18)

$^1$H-NMR: Nr. H15189, 90MHz, CDCl$_3$, α>>βNr. H15326, 90MHz, CDCl$_3$, β>>α

HPLC (anal.): Silica, EE:hexane:MeOH=72:28:0.7, flow: 1.0 ml/min.; R$_t$ (α)=10.32', R$_t$ (β)=8.73'.

HPLC (prep.): Silica, EE:hexane:MeOH=64:36:0.5, flow: 10.0 ml/min.; R$_t$ (α)=35', R$_t$ (β)=27';

4-O-(2,3,4,6-Tetra-O-benzyl β-D-glucopyranosyl) 2,3,6-tri-O-benzyl D-glucopyranosyl N,N'-di-(2-chloroethyl) phosphoric acid diamide 49 acc. to protocol B

Batch: 40 mg 47 (0.036 mmoles) 9 mg 4b (0.041 mmoles)

Yield: after column chromatography (silica, EE:PA= 60:40) and prep. HPLC 2 fractions were obtained (each a clear, colorless oil): F1: 18 mg 49β (42.5% of theory) F2: 7 mg 40α (10.9% of theory)

TLC: Silica, EE/PE=80:20, R$_f$ (α)=0.35, R$_f$(β)=0.42 C$_{65}$H$_{73}$Cl$_2$N$_2$O$_{12}$P (1176.18)

HPLC (anal.): Silica, EE:hexane:MeOH=72:28:1, flow: 1.0 ml/min. R$_t$ (α)=7.03', R$_t$ (β)=5.89';

HPLC (prep.): Silica, EE:hexane:MeOH=64:36:0.5, flow: 10.0 ml/min. R$_t$ (α)=35', R$_t$ (β)=25';

4-O-(β-D-galactopyranosyl) α-D-glucopyranosyl N,N'-di-(2-chloroethyl) phosphoric acid diamide 50α

Hydrogenation of 48α acc. to protocol C

C$_{16}$H$_{31}$Cl$_2$N$_2$O$_{12}$P (541.31)

$^1$H-NMR: 500 MHz, D$_2$O, Nr. H15701 δ=3.27–3.34 (m, 4H, 2x-CH$_2$-), 3.563 (dd, 1H, H-2', J$_{1',2}$=8.0 Hz, J$_{2',3}$= 9.8 Hz), 3.65–4.0 (m, 15H with 4H at 3.65–3.68, 2x-CH$_2$-), 4.478 (d, 1H, H-1', J$_{1',2}$=8.0 Hz), 5.623 (dd, 1H, H-1, J$_{1,2}$=3.6 Hz, J$_{1,P}$=7.8 Hz).

| FAB-MS: | Nr. MSN 14075 | | | |
|---|---|---|---|---|
| | positive | m/e = | 221, 223, 225 | (IPM+H)$^+$ |
| | | | 545, 547, 549 | (M+H)$^+$ |

4-O-(β-D-Galactopyranosyl) β-D-glucopyranosyl N,N'-di-(2-chloroethyl) phosphoric acid diamide 50β

Hydrogenation of 48β acc. to protocol C

C$_{16}$H$_{31}$Cl$_2$N$_2$O$_{12}$P (541.31)

$^1$H-NMR: 500 MHz, D$_2$O, $^1$H-$^1$H-2D-COSY, Nr. 15834 δ=3.27–3.34 (m, 4H, 2x-CH$_2$-), 3.43 (dd, 1H, H-2, J$_{1,2}$=8.0 Hz), 3.558 (dd, 1H, H-2', J$_{1',2}$=8.0 Hz, J$_{2',3}$=10.0 Hz), 3.65–3.68 (m, 4H, 2x-CH$_2$-), 3.68–3.90 (m, 8H), 3.938 (dd, 1H, J=3.4 and J=1.0 Hz), 3.989 (dd, 1H, J=1.9 and J=12.6 Hz), 4.473 (d, 1H, H-1', J$_{1',2}$=8.0 Hz), 5.049 (t, 1H, H-1, J$_{1,2}$=J$_{1,P}$=8.0 Hz).

| FAB-MS: | Nr. MSN 14076 | | | |
|---|---|---|---|---|
| | positive | m/e = | 221, 223, 225 | (IPM+H)$^+$ |
| | | | 545, 547, 549 | (M+H)$^+$ |

4-O-(β-D-glucopyranosyl) α-D-glucopyranosyl N,N'-di-(2-chlorethyl) phosphoric acid diamide 51α

Hydrogenation of 49α acc. to protocol C

C$_{16}$H$_{31}$Cl$_2$N$_2$O$_{12}$P (541.31)

$^1$H-NMR: 500 MHz, D$_2$O, $^1$H-$^1$H-2D-COSY, Nr. 15856 δ=3.27–3.32 (m, 4H, 2x-CH$_{1,2}$-), 3.333 (dd, 1H, H-2', J$_{1',2}$=7.9 Hz, J$_{2',3}$=9.4 Hz), 3.40–3.45 (m, 2H), 3.47–3.55 (m, 2H), 3.64–3.68 (m, 4H, 2x -CH$_2$-), 3.69 (dd, 1H, H-2), 3.70–3.99 (m, 6H), 4.537 (d, 1H, H-1', $J_{1',2'}$=7.9 Hz), 5.622 (dd, 1H, H-1, $J_{1,2}$=3.6 Hz, $J_{1,P}$=7.8 Hz).

| FAB-MS: | Nr. MSN 14077 |       |              |           |
|---------|---------------|-------|--------------|-----------|
|         | positive      | m/e = | 221, 223, 225 | (IPM+H)$^+$ |
|         |               |       | 545, 547     | (M+H)$^+$ |

4-O-(β-D-Glucopyranosyl) β-D-glucopyranosyl N,N'-di-(2-chloroethyl) phosphoric acid diamide 51β

Hydrogenation of 49β acc. to protocol C $C_{16}H_{31}Cl_2N_2O_{12}P$ (541.31)

$^1$H-NMR: 500 MHz, $D_2O$, $^1$H-$^1$H-2D-COSY, Nr. 15857 δ=3.27–3.32 (m, 4H, 2x-CH$_{1,2}$-), 3.33 (dd, 1H, H-2', $J_{1',2'}$= 8.0 Hz, $J_{2',3'}$≈10 Hz), 3.428 (dd, 1H, H-2, $J_{1,2}$=8.0 Hz, $J_{2,3}$=10.0 Hz), 3.44–3.54 (m, 3H), 3.64–3.68 (m, 4H, 2x-CH$_2$-), 3.69–3.72 (m, 3H), 3.745 (dd, 1H, H-6'a, $J_{5',6'a}$= 5.8 Hz, $J_{6'a,6'b}$=12.3 Hz), 3.855 (m, 1H, H-6b), 3.928 (dd, 1H, H-6'b, $J_{5',6'b}$32 2.1 Hz, $J_{6'a,6'b}$≈12.3 Hz), 3.990 (dd, 1H, H-6a, $J_{5,6a}$=2.0 Hz, $J_{6a,6b}$=12.2 Hz), 4.532 (d, 1H, H-1', $J_{1',2'}$=8.0 Hz), 5.044 (t, 1H, H-1, $J_{1,2}$=$J_{1,P}$=8.0 Hz).

| FAB-MS: | Nr. MSN 14078 |       |                |           |
|---------|---------------|-------|----------------|-----------|
|         | positive      | m/e = | 221, 223, 225  | (IPM+H)$^+$ |
|         |               |       | 545, 547, 549  | (M+H)$^+$ |

EXAMPLE 3

Maltotriose is peracetylated (using sodium acetate/acetanhydride). The product has $R_f$ 0.48, CHCl$_3$/ethylacetate 1:1 oh silica gel. From the product the 1-bromide is prepared using HBr/glacial acetic acid at 0° C. (product: $R_f$=0.58, same conditions as above). From this product the 1-alkyl-maltotrioside is prepared using allyl alcohol/Ag$_2$CO$_3$, product: $R_f$=0.60, same conditions as above) From this product alkyl-2,3,6,2',3',6',2",3",6" deca-O-benzyl-maltotrioside is prepared using benzyl chloride/KOH at 120° C. (product: $R_f$=0.51, toluene/ethyl acetate 10:1 using silica gel). After isomerization to the enol ether the latter is saponified using 1N HCl to get the 1-OH compound (product: $R_f$=0.17, toluene/ethyl acetate 10:1, using silica gel). From this product the trichloroacetimidate is prepared by reaction with NaH and trichloroacetonitrile (product: $R_{f\alpha}$0.48, same conditions as above). From this product the glycoconjugate is prepared in acetonitrile using ifosfamide mustard under reflux (product: $R_f$=0.24, ethyl acetate/hexan 6:4, using silica gel). By hydrogenation with 10% Pd/activated carbon in CH$_3$OH at ambient temperature. the benzylic groups are split off (product:$R_f$=0,22, CHCl$_3$/methanol 1:1 using silica gel).

We claim:

1. A glycoconjugate of phosphoric acid amide mustard or ifosfamide mustard having the formula

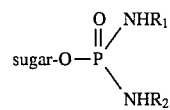

1 or

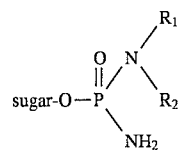

1a wherein the sugar moiety is linked to the phosphoric acid amide mustard residue (1), or to the ifosfamide mustard residue (1a), $R_1$ and $R_2$, whioh can be the same or different, denote hydrogen, $C_1$–$C_4$ allkyl or $C_1$ $C_6$ halogenoslkyl, and the sugar moiety is a mono-, dl- or polysaccharide in any existing isomeric or enantiomeric forms.

2. The glycoconjugate of claim 1, wherein $R_1$ is $C_1$–$C_4$ halogenoalkyl.

3. The glycoconjugate of claim 1, wherein $R_2$ is $C_1$–$C_4$ halogenoalkyl.

4. The glycoconjugate of claim 1, wherein $R_1$ is $C_2$ halogenoalkyl.

5. The glycoconjugate of claim 1, wherein R, is C, halogenoalkyl.

6. The glycoconjugate of claim 1, wherein $R_1$ and $R_2$ are $C_2$ halogenoalkyl.

7. The glycoconjugate of claim 6, seclected from thc group consisting of:

α-D-glucopyranosyl N,N'-di(2-chloroethyl) phosphoric acid diamide, ⊕β-D-glucopyranosyl N,N'-di(2-chloroethyl) phosphoric acid diamide, α-D-galactopyranoayl N,N'-di(2-chlorocthyl)phosphoric acid diamide, α-D-mannopyranosyl N,N'-di(2-chloroethyl) phosphoric acid diamide, β-D-mannopyranosyl N,N'-di(2-chloroethyl) phosphoric acid diamide, 4-O-(β-D-galactopyranosyl) α-D-glucopyranosyl N,N'-di(2-chloroethyl) phosphoric acid diamide, 4-O-(β-D-galactopyranosyl) N,N'-di(2-chloroethyl) phosphoric acid diamide, 4-O-(β-D-galactopyranosyl) β-D-glucopyrsnosyl N,N'-di(2-chloroethyl) phosphoric acid diamide, 4-O-(β-D-glucopyrsnoyl) α-D-glucopyranosyl N,N'-di(2-chloroethyl phosphoric acid diamide, and 4-O-(β-D-glucopyranosyl) β-D-glucopyranosyl N,N'-di(2-chloroethyl) phosphoric acid diamide.

8. A method for the preparation of a glycoconjugate of phosporic acid amide mustard or ifosfamide mustard of claim 1 which comprises conjugating a protected brominated sugar with phosphoric acid amide mustard or ifosfamide mustard, respectively, and removing the protective groups.

9. A method for treating a tumor in all animal or in a human which comprises administering an effective amount of an antitumor agent which comprises a glycoconjugate of claim 7 and a pharmaceutically acceptable carrier.

10. The method of claim 9 wherein aid tumor is selected from the group consisting of breast carcinoma, Morbus Hodgkin, and tumors in the gastrointestinal tract.

* * * * *